United States Patent
Hawkins

(10) Patent No.: US 10,813,783 B1
(45) Date of Patent: Oct. 27, 2020

(54) SPINAL ORTHOSIS

(71) Applicant: Michael Browning Hawkins, Alexandria, VA (US)

(72) Inventor: Michael Browning Hawkins, Alexandria, VA (US)

(73) Assignee: Michael Browning Hawkins, Alexandria, VA (US)

( * ) Notice: Subject to any disclaimer, the term of this patent is extended or adjusted under 35 U.S.C. 154(b) by 110 days.

(21) Appl. No.: 16/161,030

(22) Filed: Oct. 15, 2018

Related U.S. Application Data

(60) Provisional application No. 62/571,795, filed on Oct. 13, 2017.

(51) Int. Cl.
*A61F 5/02* (2006.01)

(52) U.S. Cl.
CPC .............. *A61F 5/028* (2013.01); *A61F 5/022* (2013.01)

(58) Field of Classification Search
CPC .......... A61F 5/028; A61F 5/027; A61F 5/022; A61F 5/024
See application file for complete search history.

(56) References Cited

U.S. PATENT DOCUMENTS

| | | | | |
|---|---|---|---|---|
| 2,541,587 A | * | 2/1951 | Triplett | G01R 11/02 235/91 G |
| 5,158,531 A | * | 10/1992 | Zamosky | A61F 5/024 602/19 |
| 5,387,183 A | * | 2/1995 | Jones | A61F 5/028 128/100.1 |
| 5,421,809 A | * | 6/1995 | Rise | A61F 5/028 128/876 |
| 5,690,609 A | * | 11/1997 | Heinze, III | A61F 5/028 128/115.1 |
| 6,099,490 A | * | 8/2000 | Turtzo | A61F 5/028 2/311 |
| 8,795,216 B2 | * | 8/2014 | Chang | A61F 5/024 128/876 |
| 9,808,369 B1 | * | 11/2017 | Gaylord | A61F 5/028 |
| 10,034,791 B2 | * | 7/2018 | DeLuke | G16H 40/67 |
| 2010/0268138 A1 | * | 10/2010 | Summit | A61F 5/013 602/16 |
| 2011/0230806 A1 | * | 9/2011 | Lou | A61F 5/012 602/13 |
| 2012/0022418 A1 | * | 1/2012 | Gamboa | A61F 5/028 602/19 |
| 2014/0221890 A1 | * | 8/2014 | Thibeault | A61F 5/026 602/13 |

* cited by examiner

*Primary Examiner* — Kristen Matter

(57) ABSTRACT

An improved spinal orthosis for treating scoliosis comprises a semi-rigid brace shell with a split extending from a top end to a bottom end, and a cavity to receive the torso of a wearer. The brace shell defines at least one hole. At least one strap extends inside of a portion of the brace shell, through the at least one hole and around a portion of the outside of the brace shell across the split in the brace shell. The at least one strap is tensioned and the brace shell is closed around the wearer by pulling a first end of the at least one strap and detachably fastening it to the brace shell. The tensioned strap harnesses the elastic potential energy of the closed brace shell to apply dynamic corrective forces to the area of the user's torso most proximate to the apex of the spinal curvature.

15 Claims, 15 Drawing Sheets

SPINAL ORTHOSIS

CROSS-REFERENCE TO RELATED APPLICATIONS

This application claims the benefit of U.S. Provisional Patent Application No. 62/571,795, filed 2017 Oct. 13 by the present inventor, which is hereby incorporated by reference herein in its entirety.

FIELD OF THE INVENTION

The invention relates generally to an orthopedic device, and more specifically to a spinal orthosis for providing alignment to a spine.

BACKGROUND

Prior Art

The following is a tabulation of some prior art that presently appears relevant:

U.S. Patents

| Pat. No. | Kind Code | Issue Date | Patentee |
| --- | --- | --- | --- |
| 9,398,972 | B2 | 2016 Jul. 26 | Yip et al. |
| 8,795,213 | B2 | 2014 Aug. 5 | Mills |
| 7,967,767 | B2 | 2011 Jun. 28 | Ogilvie |
| 7,766,850 | B2 | 2010 Aug. 3 | Simanovsky |
| 5,599,286 | A | 1997 Feb. 4 | Labelle et al. |
| 5,503,621 | A | 1996 Apr. 2 | Miller |
| 5,256,135 | A | 1993 Oct. 26 | Avihod |
| 5,012,798 | | 1991 May 7 | Graf et al. |
| 4,688,558 | | 1987 Aug. 25 | Hooper, Jr. et al. |
| 4,285,336 | | 1981 Aug. 25 | Oebser et al. |
| 4,245,627 | | 1981 Jan. 20 | Mignard |
| 4,230,101 | | 1980 Oct. 28 | Gold |
| 4,202,327 | | 1980 May 13 | Glancy |
| 3,282,264 | | 1966 Nov. 1 | N.C. Connelly |
| 3,095,875 | | 1963 Jul. 2 | I. Davidson et al. |
| 1,803,556 | | 1931 May 5 | J. J. Nugent |
| 492,903 | | 1893 Mar. 7 | G. Gerlitz |

U.S. Pat. application Publications

| Publication Number | Kind Code | Publ. Date | Applicant |
| --- | --- | --- | --- |
| 201701079828 | A1 | 2017 Mar. 23 | LIM Innovations, Inc. |
| 20150297387 | A1 | 2015 Oct. 22 | Thompson et al. |
| 20140296759 | A1 | 2014 Oct. 2 | Matthews |
| 20130303955 | A1 | 2013 Nov. 14 | Beitl |

Foreign Patent Documents

| Foreign Doc. No. | Country Code | Kind Code | Publ. Dt | App or Patentee |
| --- | --- | --- | --- | --- |
| 2017204429 | KR | A1 | 2017 Nov. 30 | Standingtall Co Ltd |
| 722839 | NZ | A | 2017 Mar. 31 | Aspen Medical Partners LLC |
| 205814503U | CN | U | 2016 Dec. 21 | Liao Jingjian |
| 2014-087381 | JP | A | 2014 May 15 | Nagano Gishi KK |
| 2005-137448 | JP | A | 2005 Feb. 6 | Nagano Gishi KK |
| 20040103300 | KR | A | 2004 Dec. 8 | Ms Meditec |
| 2131713 | RU | C1 | 1999 Jun. 20 | Ol Khovikov |

Nonpatent Literature Documents

John D. Hsu, John W. Michael, John R. Fisk, *AAOS Atlas of Orthoses and Assistive Devices*, "Chapter 2: Spinal Orthoses", Elsevier Health Sciences, Jan. 1, 2008

Rigo and Jelčič. Brace technology thematic series: the 3D. Scoliosis and Spinal Disorders (2017) 12:10

Scoliosis, a lateral and rotational deformity of the spine, is often treated during childhood or adolescence with a spinal orthosis if the severity of the scoliosis curve, measured by the Cobb angle, is greater than 20 degrees. Many types of spinal orthoses intended to treat scoliosis exist; however, there is a current need for improvement in such spinal orthoses.

Many of the types of spinal orthosis heretofore utilized for treatment of scoliosis have been static orthoses. Some past designs of this type are merely supportive and provide little, if any, improvement in spine alignment when applied. Such supportive types of static orthoses have been used as a preventive measure to maintain the present status of the scoliosis condition and try to stop the condition from becoming more severe. Such types of devices are often cylindrical forms that are shaped to a normal, or symmetric contour and usually compress portions of the trunk affected by the spinal curvature.

As the designs of static spinal orthoses for scoliosis have progressed, various types of static spinal orthoses have been designed with the intent of applying asymmetric forces to the body's exterior surface to move the spine into improved alignment, categorized as corrective orthoses. However, these designs have limitations and shortcomings.

Corrective orthoses are often constructed of rigid to semi-rigid material and are often asymmetric in shape and contour with indentations or pads in areas of the orthosis corresponding to the apex of the spinal curvature, and additional space within the orthosis where the wearer's body moves to achieve improved spinal alignment. These orthoses are limited in the degree to which they can improve alignment due to their static characteristics. During normal daily wear the orthosis has no ability to independently move the wearer's spine any further into alignment than in the last position in which the orthosis was set or tightened. There are upper limits to the degree this type of orthosis can be further tightened during daily wear due to the need for expansion during the wearer's inhalation phase of the respiratory cycle. Therefore, wearers are resigned to tightening the device only as far as their maximum torso dimensions during their respiratory cycle will allow. During points in their respiratory cycle when their torso dimensions are smaller, the corrective forces reduce and alignment is lost.

Furthermore, when a wearer is in a horizontal position at rest, the soft tissue surrounding the spinal column is in a relaxed state in which the deformed areas of the spine may yield to corrective forces to a much greater degree than when the wearer is active and upright. However, a static spinal orthosis is unable to take advantage of this occurrence as it is not able to provide corrective forces across any range of movement or change in position of the wearer's torso.

Dynamic spinal orthoses are another type of orthoses intended for the treatment of scoliosis that are capable of providing directed corrective forces on the external surface of the wearer's body through a range of movement or change in position without additional adjustment. The prior art contains examples of such dynamic spinal orthoses including U.S. Pat. No. 4,202,327. Orthoses of this type may rely on additional mechanical components purposed for creating force through a range of movement. They often require relatively many components and as a result are usually more bulky and are more visually apparent under the wearer's clothing. This is a major deterrent to wearer's compliance with daily use of an orthosis as patients prefer orthoses that can be worn inconspicuously under their clothes. Additionally, the cost of the additional, more sophisticated components and the additional time of manufacture make this type of brace in the prior art costly to manufacture.

Some orthoses described as being dynamic rely on metal components as a support structure around which the functional aspects of the brace may operate. Orthoses that comprise metal or rigid structural components such as a rod of relatively significant size have become an object of distaste for wearers and, in modern times, a reason for which many child and adolescent wearers will reject the use of a brace and become non-compliant. Additionally, wearer's tend to reject orthoses comprising mechanical components with straight lines and external corners that can be visualized through their clothing by bystanders. This is one reason why the dynamic braces in the prior art are not popular in many clinical settings in our current society.

Prior art according to U.S. Pat. No. 7,967,767 comprises rigid components that do not wrap completely around the wearer's torso thus sacrificing stiffness due to the open anterior portion of this design. This design limits the extent to which the system can resist torsional and bending moments placed on it by the torso of a wearer with a misaligned spine and thus limits the degree to which this type of orthoses can correctively align a wearer's spine. Additionally, U.S. Pat. No. 7,967,767 is labelled as "dynamic"; however, this spinal orthosis contains no mechanism to continually apply corrective forces to a wearer throughout movement and change in wearer position without further adjustment. This design lacks the ability to adjust to the positions of the user while wearing the orthosis without a third party manually adjusting the dimensions of the brace, and therefore lacks the essentials of a truly dynamic brace.

Some devices intended for the corrective alignment of scoliotic spines are supple, comprised substantially of soft, or textile material or woven fabric, the features of which do not retain a general shape but continuously deform when force is applied. I have observed that it is not possible to apply forces to the external surface of the human body in a defined and predetermined vector sufficient to align a wearer's spine relying substantially on supple, or soft textile based woven materials. With no substantial measure of stiffness with which to resist compressive and torsional forces, and bending moments, a spinal orthosis has no structure from which to produce a directed force that can move one portion of a wearer's spine into alignment, while stabilizing portions of the spine above and below the scoliosis curve intended for alignment.

Additionally, this type of orthosis has to rely on wrapping over the wearer's shoulder to remain oriented vertically on the wearer's body. Tensioning the fabric of this type of orthosis in an attempt to create corrective forces on the spine, unfortunately, produces a compressive force on the spine through the wearer's shoulder complex and upper ribs over which the orthosis is wrapped. This compressive force is counterproductive to the alignment of a scoliotic spine. It is also apparent through clinical observation that orthoses comprised substantially of flexible material substantially conform to the deformities on the body's surface that result from the spinal deformities, and are ineffective at aligning the scoliotic spine and improving postural deformities that result therefrom.

Any spinal orthoses in the prior art that extend superiorly past the height of the wearer's shoulder when donned possess an inherent barrier to wearing compliance. Many orthosis wearers like the option of wearing clothes that only partially cover the shoulders or are low cut around the collar. If an orthosis comes to a height in which it is no longer covered by such clothing, the wearer will not consider wearing that particular piece of clothing. This presents another point at which wearing an orthosis affects a wearer's regular routine and preferences and therefore deters compliance.

Some spinal orthoses, including the prior art according to U.S. Pat. No. 7,766,850 attempt to influence scoliotic curves present in a wearer's spine through securing to the pelvis and mid-thoracic area using two isolated shell components linked together by a rod with only one point of connection to each shell component. This type of design sacrifices a significant amount of stiffness in resistance to torsional forces created by the rotational deformity of scoliosis. The single connection point between each shell and the posterior rod is a weak point in the system. The aspect of each shell component in the area of each shell's connection to the rod experiences a significant amount of deformation when attempting to resist the torsion and bending moments placed on the system by the wearer and renders the orthosis ineffective. By increasing the thickness of the material used for the shell components in an attempt to decrease the degree of deformation that take place in this area of the brace shell, the likelihood of wearing compliance decreases as wearer's do not prefer spinal orthosis with shells or shell components that are relatively thick.

Furthermore, this type of spinal orthosis ignores the fact that scoliosis can, in many cases, manifest as a spinal curve with an apex in the lower thoracic or upper lumbar spine where this orthosis does not interface with the user. This approach provides no method of applying direct contact to areas of the body most proximate to a lower thoracic or upper lumbar curve apex. This orthosis according to its own description would be rendered completely ineffective with a spine curve apex positioned between the two shell components. In any case, three point pressure systems have been found to be effective characteristics of spinal orthoses for aligning a wearer's spine which this type of spinal orthosis is incapable of harnessing.

Lastly, the design of many spinal orthoses in prior art rely on three or more straps to secure the brace on the wearer. With relatively many straps, these orthoses take a relatively long time to don. This is a point which deters users from donning an orthosis after completing activities requiring doffing of an orthosis thereby reducing compliance with prescribed wearing hours.

SUMMARY

A spinal orthosis according to the present disclosure comprises a brace shell that extends from a top end to a bottom end, has a split that extends from the top end to the bottom end, has a cavity configured to receive a torso of a wearer, and defines at least one hole that extends radially from the cavity. The spinal orthosis further comprises at least one strap configured to extend circumferentially inside of at least a portion of the brace shell. The at least one strap is configured to extend through the at least one hole to wrap circumferentially around at least a portion of the outside of the brace shell. The at least one strap comprises a first end and a second end. The second end of the at least one strap is configured to fasten to the brace shell, and the first end is configured to detachably fasten to the brace shell. When tensioning the at least one strap the portion of the at least one strap configured to extend circumferentially inside of at least a portion of the brace shell is urged toward the center of the brace shell cavity, and the split in the brace shell is urged into a relatively closed position.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

BRIEF DESCRIPTION OF THE DRAWINGS

In order that the features, aspects, and advantages of a spinal orthosis may be more readily understood, reference will now be made to the accompanying drawings which illustrate embodiments of the spinal orthosis.

DETAILED DESCRIPTION OF VARIOUS EMBODIMENTS

A. Advantages

Figure 1:
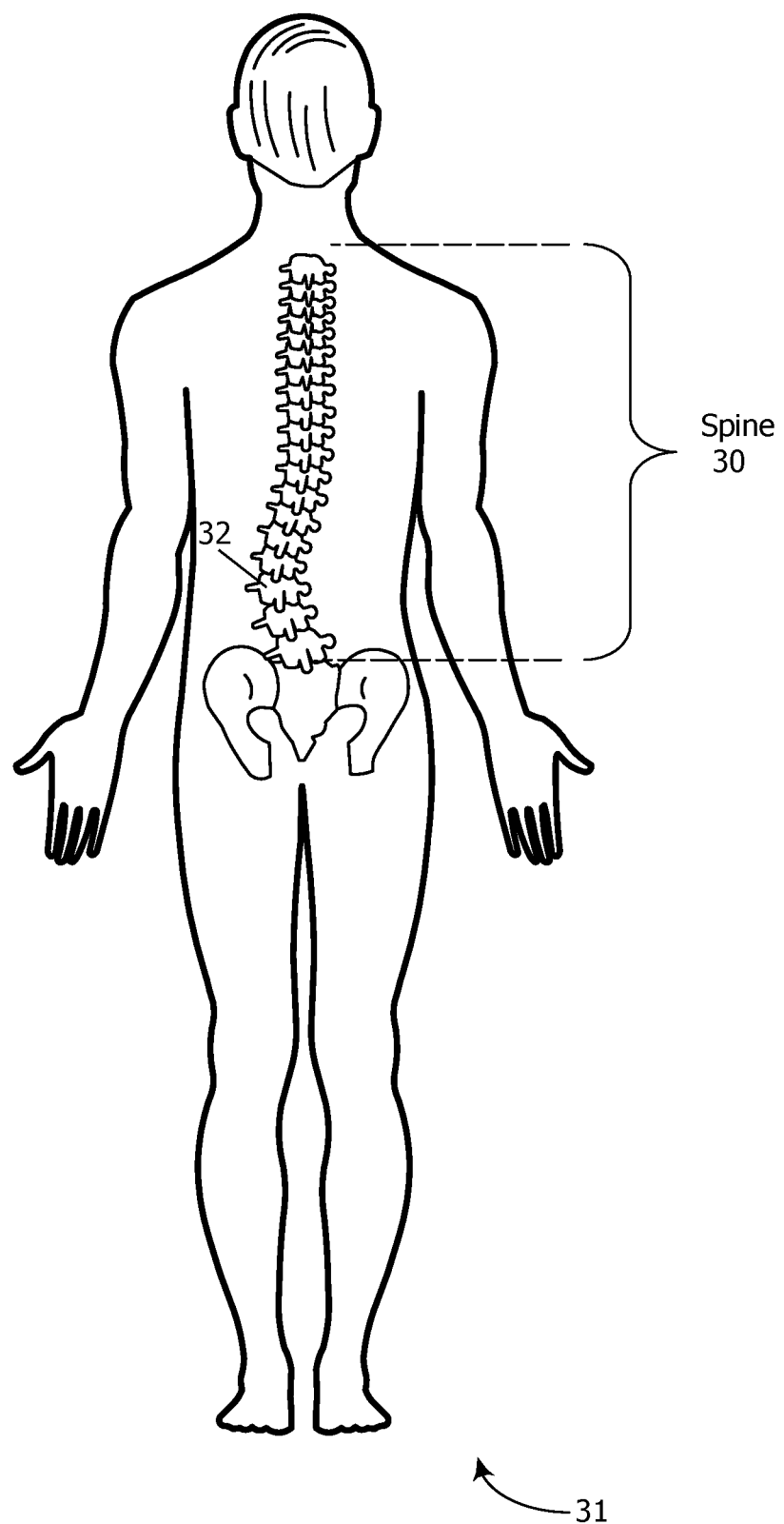
FIG. 1 is a rear view of a scoliosis condition comprising a single left curve that may provide an opportunity for correcting spine alignment in accordance with aspects of the present disclosure.
Figure 2:
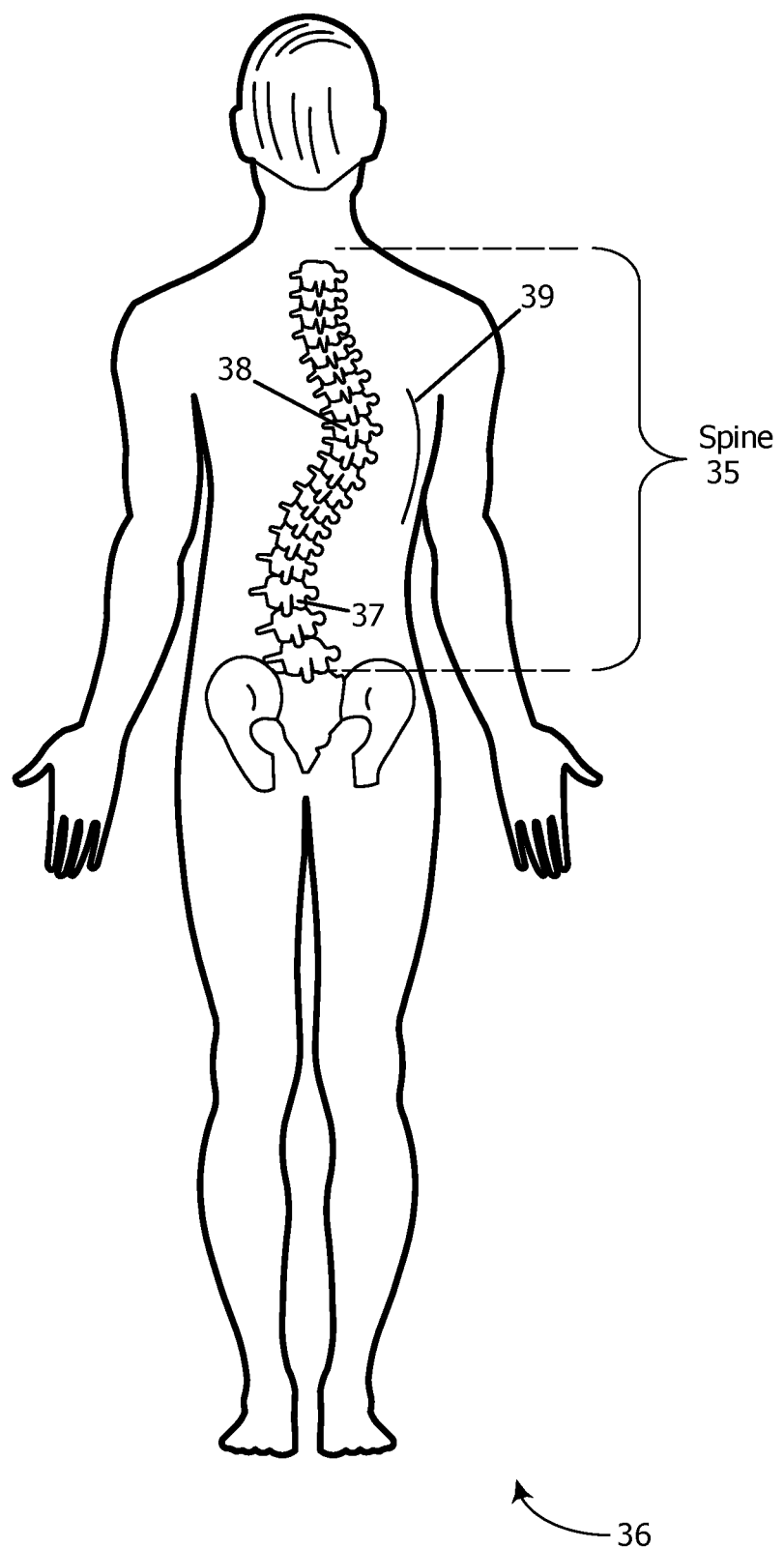
FIG. 2 is a rear view of a scoliosis condition comprising a double curve that may provide an opportunity for correcting spine alignment in accordance with aspects of the present disclosure.

The spinal orthosis according to the present disclosure presents an advantage over prior art in harnessing the inherent properties of a low profile brace shell, specifically the property of storing elastic potential energy when bent, to create and maintain corrective dynamic tension on at least one strap. The configuration of this spinal orthosis requires only a minimal number of individual components exposed on the outer surface of a single piece brace shell to maintain dynamic corrective forces on the wearer's torso. The dynamic corrective forces are maintained during changes in body position, torso dimensions, and across a range of movement enabling the device to apply corrective forces on the body after a degree of correction has previously been achieved without the need for adjustment to the brace shell or hardware thereon.

The spinal orthosis presents these advantages while maintaining a minimal number of straps and, with no additional hardware purposed for sustaining strap tension such that the orthosis is relatively inconspicuous when worn under clothing resulting in compliance to prescribed wear time. Components of relative stiffness comprising this orthosis are of organic shape and contour which are the preference of wearer's and thereby increase the likelihood of wearing compliance.

The orthosis harnesses a three-point pressure system which is necessary for correcting alignment of a spinal curvature while stabilizing the portions of the spine superior and inferior to the apex of the spinal curvature. The at least one strap is configured to provide spinal alignment via contact with the body's surface in areas most proximate the apex of the scoliotic curve and dynamically maintain spinal alignment. Once donned, corrective strap tension and spinal alignment is maintained by one continuous brace shell that wraps around the wearer's torso and closes providing adequate stiffness to resist torsional and compressive forces, and bending moments placed on the orthosis by the wearer's torso.

The cost, both in money and time, of fabricating an embodiment of the present invention is relatively small due to its one piece brace shell configuration and the simplicity, and cost of the other required components.

B. Overview

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

A better understanding of different embodiments of the invention may be had from the following description read with the accompanying drawings in which like reference characters refer to like elements.

For further ease of understanding the embodiments of an orthopedic device in the exemplary form of a spinal orthosis and variants as disclosed, a description of a few terms is necessary. As used, the term "posterior" has its ordinary meaning and refers to a location behind or to the rear of another location. The term "anterior" has its ordinary meaning and refers to a location ahead of or to the front of another location. The term "superior" has its ordinary meaning and refers to a location above or over top of another location. The term "inferior" has its ordinary meaning and refers to a location below or under another location. The term "Right" and "Left" have their meaning relative to the orthopedic device wearer's anatomical right and left. The embodiments of the orthosis are particularly referred to as corresponding to the sagittal plane. The anatomical terms described herein are not intended to detract from the normal understanding of such terms as readily understood by one of ordinary skill in the art of orthopedics.

The terms "flexible" and "resilient" may be used to distinguish characteristics of portions of certain features of the orthopedic device. The term "flexible" should denote that features are capable of repeated bending such that the features may be bent into retained shapes, and continuously deform when force is applied. The term "resilient" may qualify such flexible features as generally returning to an initial general shape without permanent deformation. As for the term "semi-rigid," this term may be used to connote properties of support members or shells that provide stiffness, support and are free-standing; however such support members or shells may have some degree of flexibility and resiliency.

The embodiments of the disclosure are adapted for a human body, and may be dimensioned to accommodate different types, shapes and sizes of human body sizes and contours. For explanatory purposes, the orthosis embodiments described are referred to as corresponding to different sections and features of a body and are denoted by general anatomical terms for the human body.

C. Various Embodiments of the Spinal Orthosis

Figure 3:
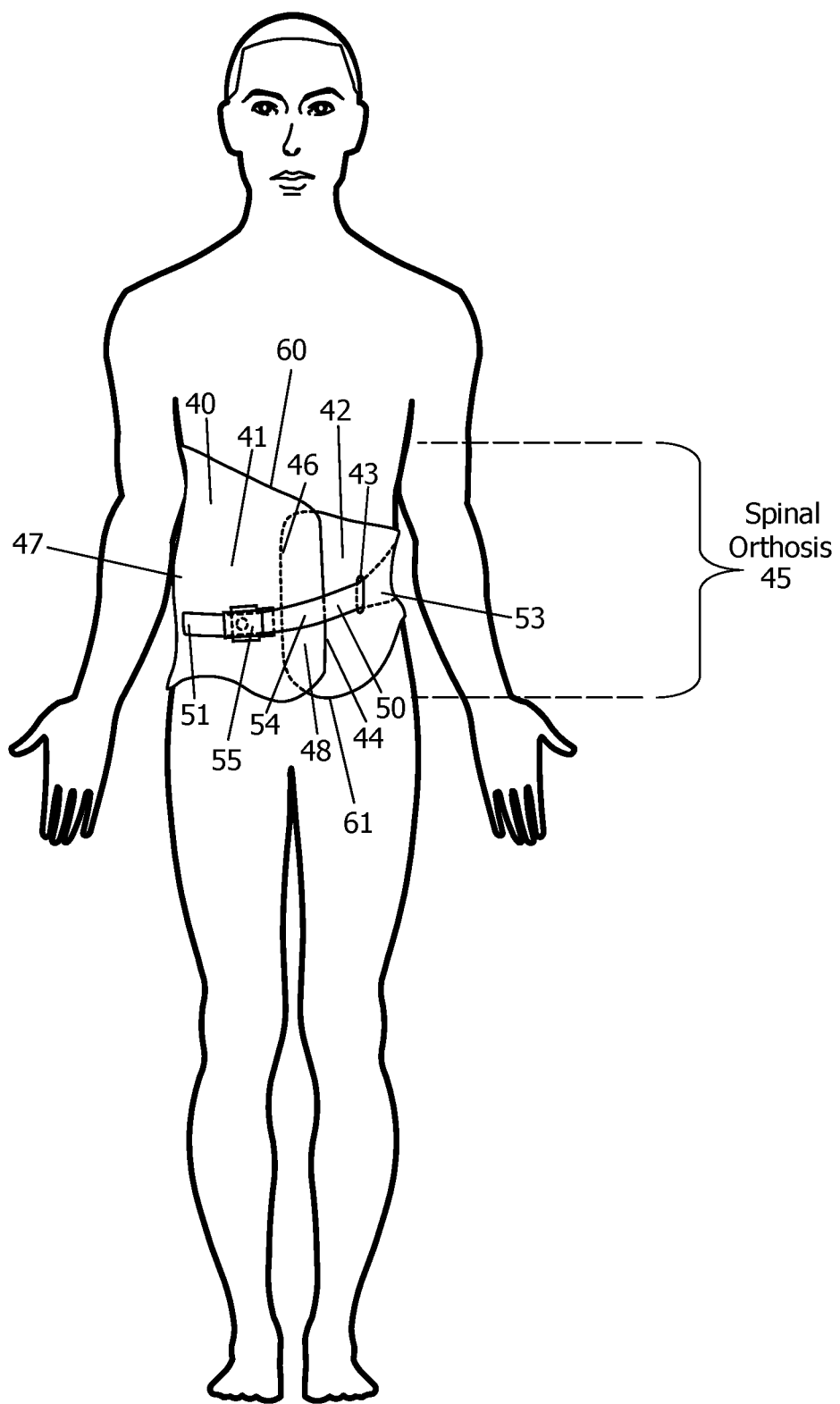
FIG. 3 is a front view of an embodiment of a spinal orthosis on a wearer.
Figure 4:
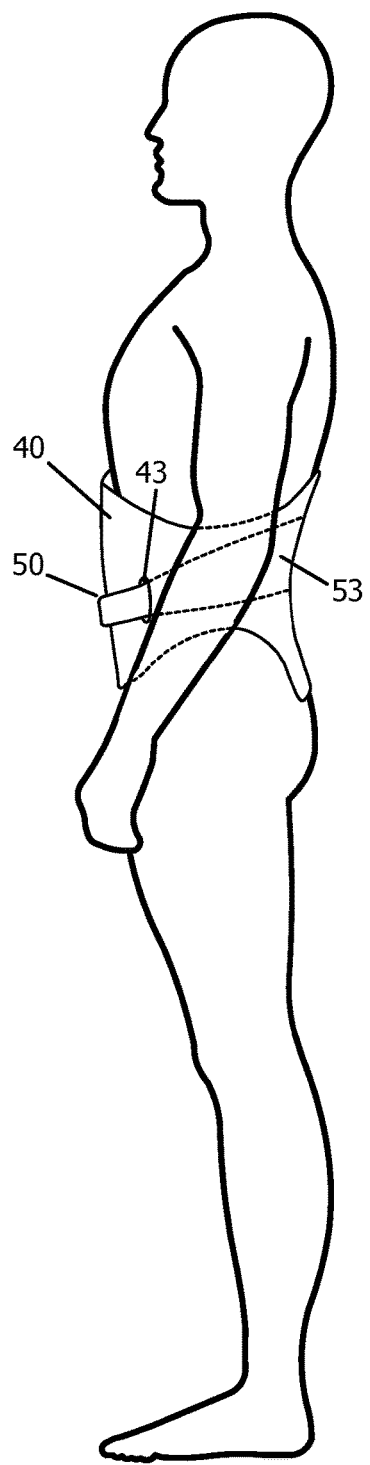
FIG. 4 is a side view of the spinal orthosis embodiment of FIG. 3 on a wearer.
Figure 5:
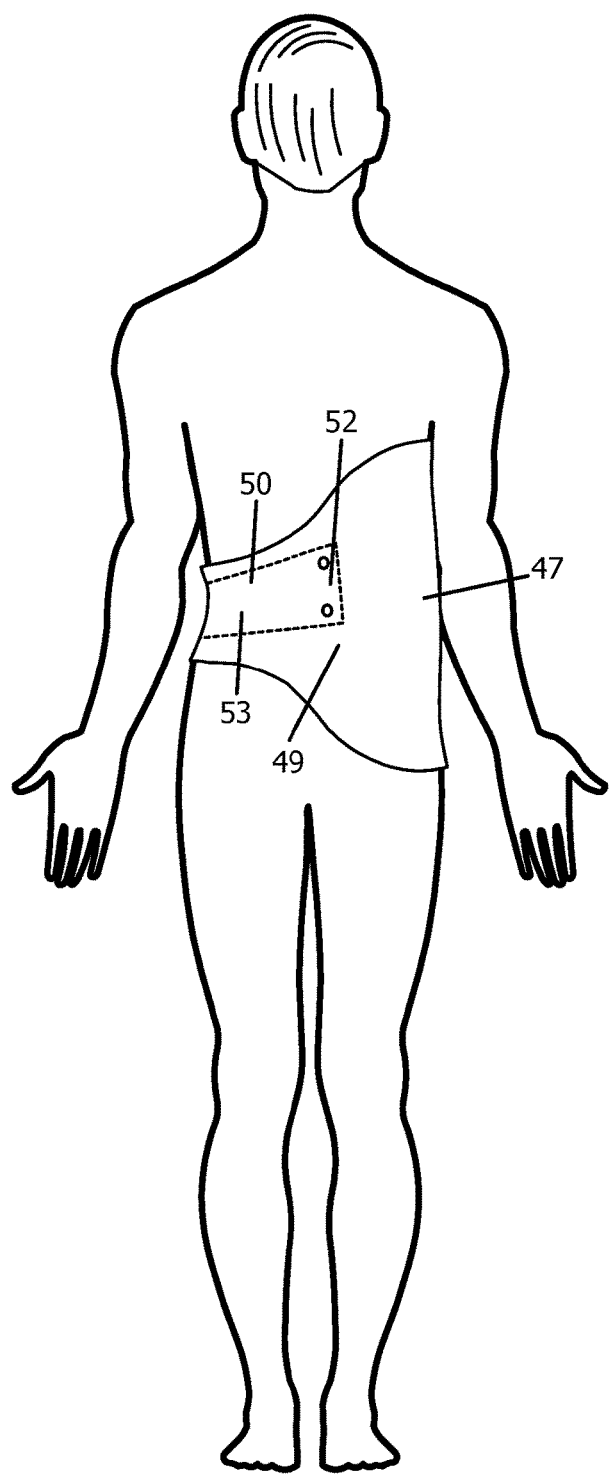
FIG. 5 is a rear view of the spinal orthosis embodiment of FIG. 3 on a wearer.

Under an embodiment shown in FIGS. 3-5 a spinal orthosis 45 is provided, among other functions, for improving the alignment of a scoliosis condition 31 in the frontal, sagittal and transverse planes toward that of a physiologically normal spine.

The orthosis 45 includes a brace shell 40, and a first strap 50, having a first end 51 and a second end 52. The brace shell has a cavity 90 and defines a first hole 43 extending radially from the cavity. The first strap 50 extends circumferentially through a portion of the inside of the brace shell through a first hole 43, defined by the brace shell 40, to extend circumferentially around a portion of the outside of the brace shell 40. The first strap 50 may be fashioned of one of many different flexible to semi-flexible and relatively inelastic materials including but not limited to nylon webbing or polyester webbing.

The brace shell 40 may be composed of one or more of many materials that possess semi-rigid characteristics; characteristics of which include resiliency and a limited degree of flexibility. Such semi-rigid materials bend when force is applied and return to an initial shape without permanent deformation. Appropriate materials for this application are capable of storing elastic potential energy when bent, capable of providing support, and capable of free-standing. Materials possessing semi-rigid characteristics which may comprise the brace shell 40 include but are not limited to polypropylene, high density polyethylene, co-polymer (composed of a blend of polypropylene and polyethylene), and other plastics, fiberglass composites, and carbon fiber composites, and other carbon based, and mineral based composites.

The brace shell comprises a cavity 90 in which the wearer's torso resides when the spinal orthosis is applied. The brace shell comprises a top end 60 and bottom end 61, each end having an opening from which the wearer's shoulders, neck, and pelvis extend. The brace shell has an anterior 48 and posterior portion 49. The brace shell comprises a split 91 extending from the top end 60 to the bottom end 61 on the anterior portion of the brace shell with which the brace shell 40 may be opened to receive the wearer's torso. The anterior portion of the brace shell is divided into a right side 41 and left side 42 by the split 91 in the brace shell 40. The right and left side of the anterior portion of the brace shell 41 and 42 each have a border 44, 46 comprising the edge of each side of the anterior portion of the brace shell that meets the split 91 extending from the top end 60 to the bottom end 61.

In a relaxed state the brace shell is open 92 wherein the border of each of the right 44 and left 46 side of the anterior portion of the brace are separated. In a relaxed state the brace shell 40 cross-section at any height of the brace is substantially "C"-shaped; the open portion of the "C"-shape representing the open split 91 in the anterior portion 48 of the brace shell 40. The brace shell 40 resists being flexed into a relatively closed position 94 in which the borders of the right 44 and the left 46 side of the anterior portion 48 of the brace shell 40 are closer to each other than in the brace shell's relaxed position 92.

The brace shell 40 is shaped to fit around a wearer's torso and a portion of the wearer's upper pelvis. Furthermore, the brace shell 40 is shaped to provide the upper and lower points of counter-force in a 3-point system of forces in which the brace shell 40 stabilizes the portions of the spine above and below the spinal curvature in order for a middle contact point to move the curved portion of the spine into alignment. The process of fabricating a brace shell 40 according to specifications such as the previous description is well known to those skilled in the art. In this embodiment, a tensioned strap 50 is configured to be the middle point in the 3-point system of forces, providing the corrective force to the apex of the spinal curvature.

The first hole 43, defined by the brace shell 40, may be slot shaped to allow the first strap 50 to slide through the hole with the strap's cross-sectional shape remaining substantially unchanged as it slides through the slot shaped hole 43. The process of creating a hole in a brace shell 40 of a prescribed shape in a prescribed location is well known to those skilled in the art.

The second end of the first strap 52 fastens to the posterior portion of the brace shell 49 at substantially the location of the superior end plate of the apical vertebrae of the scoliosis curve to which the first strap is intended to align (the term "location" intended to represent the location on the brace shell 40 corresponding the location of the described anatomical feature when the brace shell is fit around the wearer's torso).

The first strap 50 is then routed circumferentially around a left inner portion of the brace shell through the first hole 43. The location of the first hole 43 in the left anterior portion of the brace shell is determined by: placing the hole 43 at a location corresponding to the anterolateral aspect of the wearer's left rib that articulates with the apical vertebrae if the apical vertebrae is a thoracic vertebrae above T11; or, placing the hole at a location corresponding to just below the anterolateral aspect of the tenth left rib if the apical vertebrae is a lumbar vertebrae or thoracic vertebrae below T10.

According to the aforementioned, in the case of a thoracic curve apex, the first hole 43 will be located in the brace shell 40 at a height lower than that at which the second end 52 of the first strap is fastened to the brace shell 40 such that the orientation of the portion of the first strap located inside the brace shell 53 is substantially in the shape of a helix.

The first strap 50 is tensioned by pulling its first end 51, which extends out of the first hole, toward the right side 41 of the anterior portion of the brace, relatively closing the split in the brace 93. A portion of the first strap 54 extends around the outside of a portion of the left 42 and the right sides 41 of the anterior portion of the brace shell bridging the split 91 in the brace shell 40.

The first strap's orientation, when configured according to the aforementioned details, provides a corrective force in an anteromedial direction when the strap 50 is tensioned and fastened at its first end 51. The anteromedial force derotates the spine 30 and translates the spine 30 medially at the apex 32 of the spinal curvature, thereby improving spine alignment.

The first strap's first end 51 detachably fastens to the brace shell 40 on the right side 41 of the anterior portion of the brace shell in a location reachable by the first strap 50 without substantially deviating from its path initiated inside the brace shell 40. Numerous means of fastening the strap's first end 51 to the brace shell 40 are readily available and well known to those skilled in the art. Types of fasteners that allow a strap to be routed through the fastener and further tensioned by pulling the end of the strap through the fastener prior to securing the strap are preferred in this application since such fasteners would act as a pulley, closing a split in a brace shell while pulling the strap. One example of, and not an exhaustive list of such a fastener is a cam buckle 55.

When the first strap 50 is tensioned and the first end 51 fastened, an inner surface of the portion of the first strap 53 located inside the brace shell interfaces with the wearer's torso for the purpose of moving the misaligned portion of the wearer's spine toward the opposite side of the brace shell cavity 90 into alignment. The brace shell is shaped to provide adequate space 47 on the side of the brace shell cavity opposite the portion of the first strap 53 located inside the brace shell in order for the wearer's torso to move, unimpeded, into a position of spinal alignment. The process of shaping brace shells with additional space 47 within specific areas of the brace shell cavity 90 to provide space for the wearer's torso to move into a position of improved alignment is well known to those skilled in the art.

With the first strap 50 tensioned and the first end 51 thereof fastened to the right side 41 of the anterior portion of the brace shell with the brace shell 40 in a relatively closed position 94 around the wearer's torso, the portion of the first strap that interfaces with the wearer's torso maintains pressure against the surface of the wearer's torso independent of the wearer's bodily functions that change the diameter of the wearer's torso such as breathing.

Figure 22:
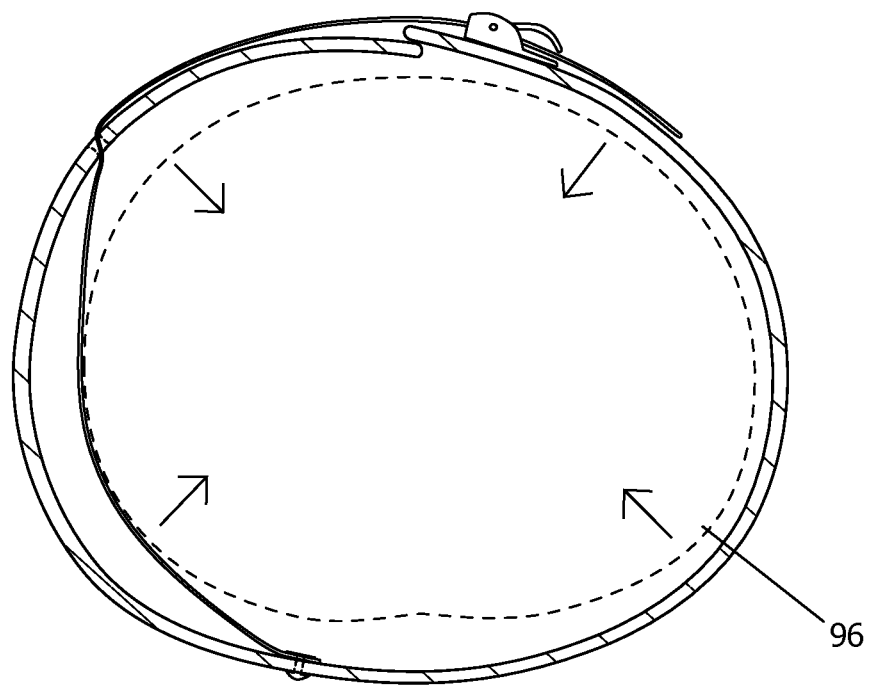
FIG. 22 is a cross-sectional view from a top perspective of the spinal orthosis embodiment of FIG. 21 around a representation of a wearer's torso dimensions upon exhalation.

The wearer's exhalation decreases the wearer's torso diameter 96, thereby decreasing tension in the first strap 50, and the first strap 50 is drawn from its first end 51 by the stored elastic potential energy of the brace shell 40 as the brace shell 40 springs toward an open position as depicted in FIG. 22. As the brace shell 40 relatively opens, a portion of the first strap 50 is pulled through the first hole 43 toward the outside of the brace shell 40, thereby shortening the length of the first strap 53 extending inside the brace shell between the second end 52 of the first strap and the first hole 43, resulting in an increase in the brace shell 40 diameter.

Figure 21:
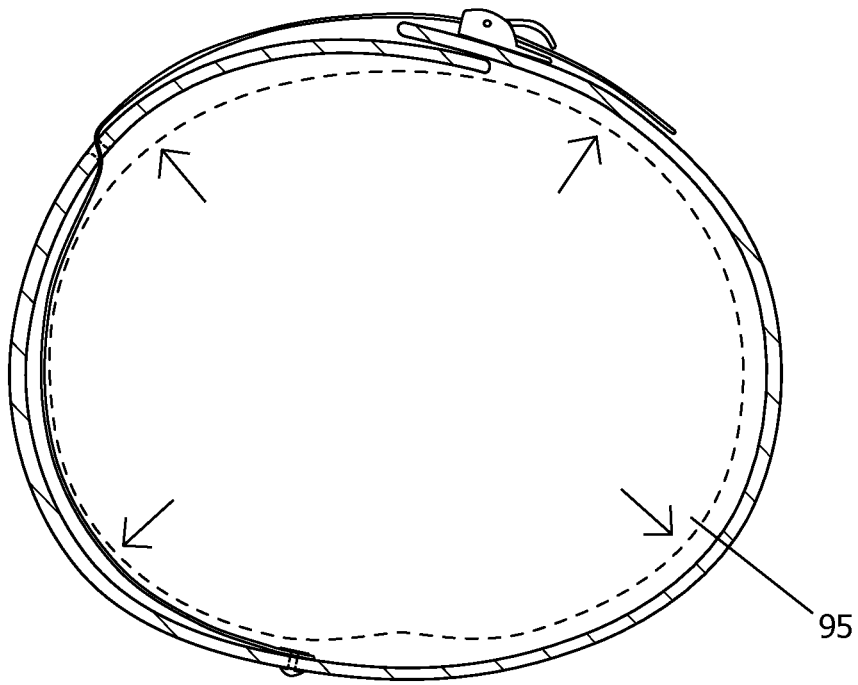
FIG. 21 is a cross sectional view from a top perspective of the spinal orthosis embodiment of FIG. 3 around a representation of a wearer's torso dimensions upon inhalation.

The wearer's inhalation increases the wearer's torso diameter 95, thereby increasing tension in the first strap 50 from inside the brace shell 40. With additional tension pulling from inside the brace shell, the first strap 50 is pulled into brace shell cavity 90 through the first hole 43 forcing a relative closure of the brace shell's split 91, thereby increasing the elastic potential energy of the brace shell as depicted in FIG. 21

Some embodiment of the spinal orthosis as shown in FIGS. 3-5 may be advantageous when applied to treating patients suffering from scoliosis 31 whose spine 30 has a single left curve having a left apex 32. This embodiment may also provide satisfactory treatment for other conditions and spinal deformations.

Figure 6:
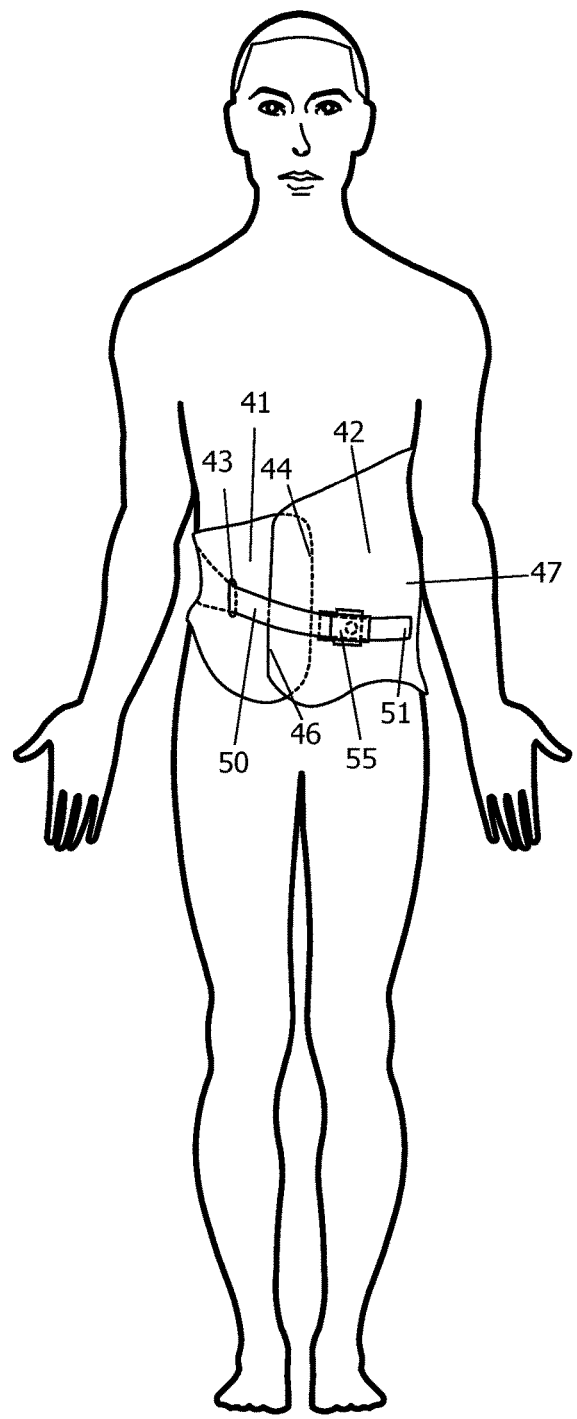
FIG. 6 is a front view of an embodiment of a spinal orthosis on a wearer depicting a mirrored configuration relative to the embodiment of FIG. 3.
Figure 7:
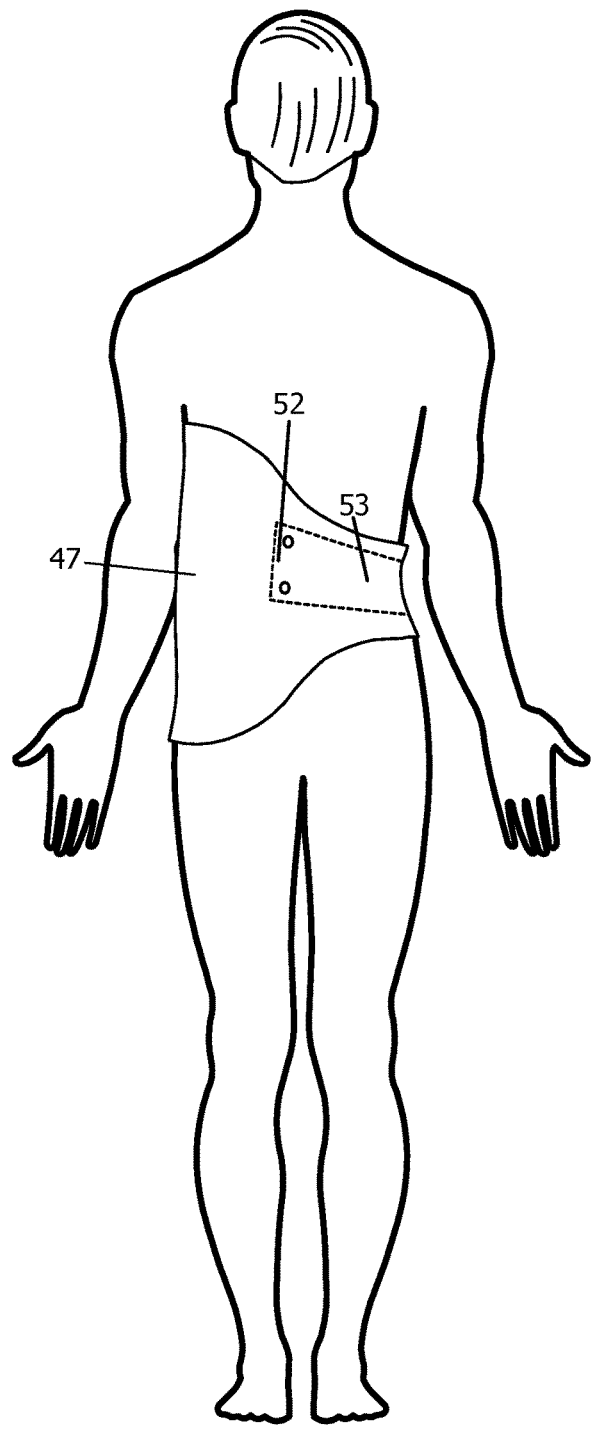
FIG. 7 is a rear view of the spinal orthosis embodiment of FIG. 6 on a wearer.

FIGS. 6-7 depict an adjustment to the spinal orthosis relative to the embodiment of the spinal orthosis in FIGS. 3-5 wherein each feature and component of the embodiment in FIGS. 3-5 is mirrored including but not limited to the first strap 50, the first hole 43, the location at which the first strap's first end 51 fastens to the brace shell 55, and the brace shell properties, shape, relative proportions, and features. The sagittal plane serves as the mirror plane for this depiction.

This embodiment of the spinal orthosis may be advantageous for treatment of wearers with a single right scoliosis curve having a right apex. This embodiment is worn by the wearer in a manner mirroring that of the embodiment in FIGS. 3-5 wherein the first strap 50 is configured to interface with the right side of the wearer's torso. This embodiment may also provide satisfactory treatment for other conditions and spinal deformations.

Figure 8:
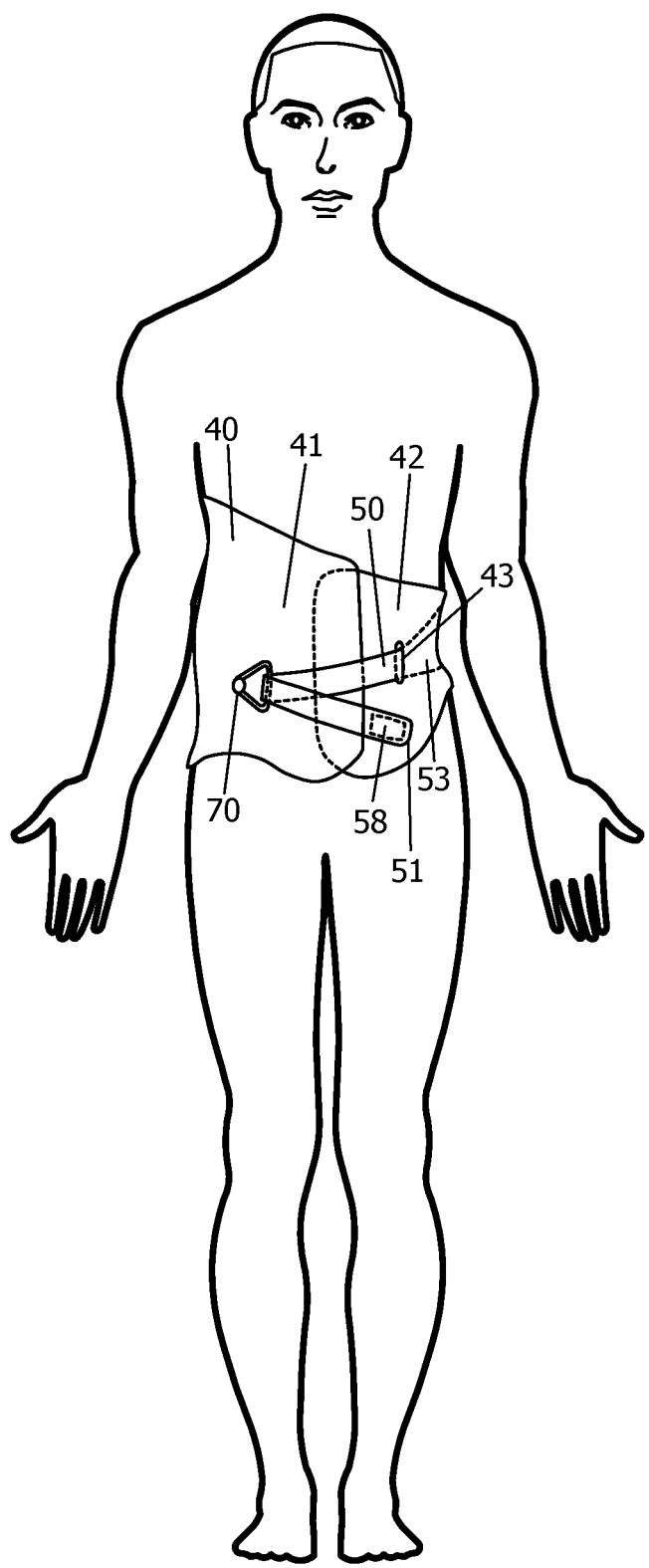
FIG. 8 is a front view of an embodiment of a spinal orthosis on a wearer in which the first strap redirects through a first bracket.

FIG. 8 depicts adjustment of the spinal orthosis relative to the embodiment in FIGS. 3-5 wherein the first strap 50 extends through the first hole 43, being located on the left side 42 of the anterior portion of the brace shell, across the brace shell split 91, to the right side 41 of the anterior portion of the brace shell and then redirects through a first bracket 70 back across the brace shell split 91 to the left side 42 of the anterior portion of the brace shell where it detachably fastens to the brace shell 40.

The first bracket 70 is fastened to the right side of the anterior portion 41 of the brace shell in a location reachable by the first strap 50 without substantially deviating from its path initiated inside the brace shell 40. Numerous means of fastening the first strap's first end 51 to the brace shell 40 in this embodiment are available and well known to those skilled in the art. Types of fasteners appropriate for use in this application include but are not limited to buckles, and hook and loop material fasteners 58.

The embodiment in FIG. 8 may require relatively less strength to close the brace shell split 91 by pulling and fastening the first strap's first end 51 as a result of the first strap's redirection and extra length. This embodiment of the spinal orthosis may be advantageous for treatment of a single left scoliosis curve in wearers who possess relatively less upper body strength such as those wearers who are younger or who may be of relatively smaller size. This embodiment may also provide satisfactory treatment for other conditions and spinal deformations.

Figure 9:
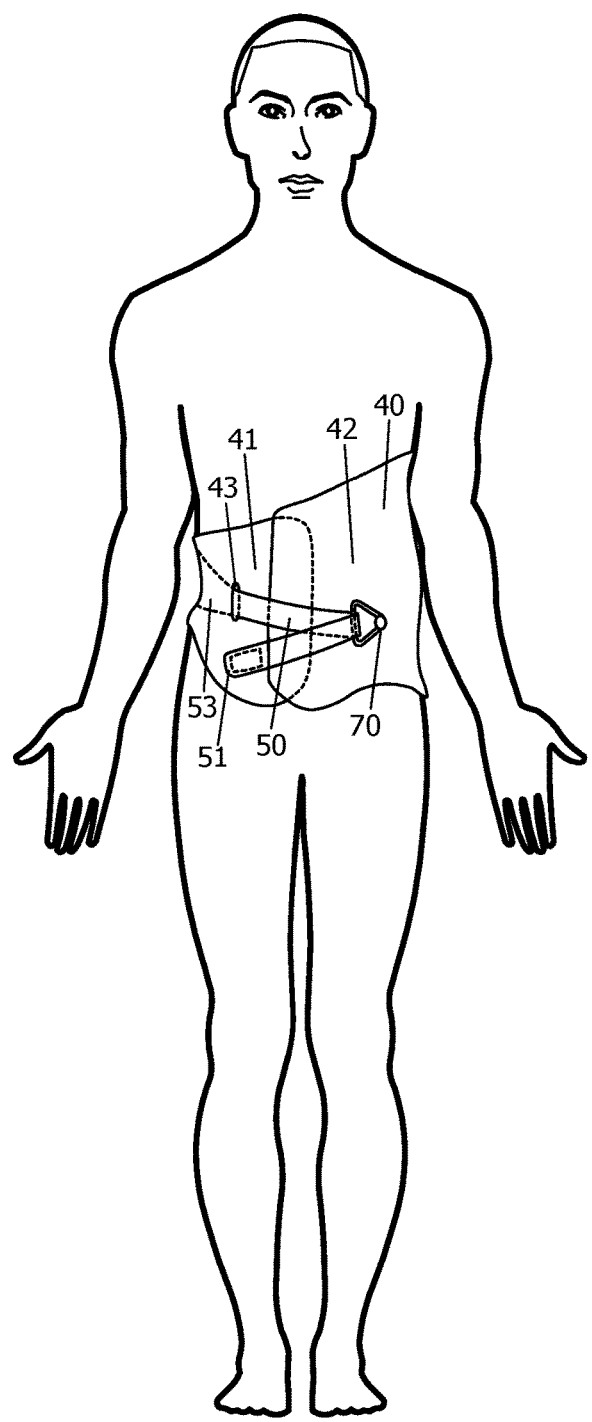
FIG. 9 is a front view of an embodiment of a spinal orthosis on a wearer depicting a mirrored configuration relative to the embodiment of FIG. 8.
Figure 10:
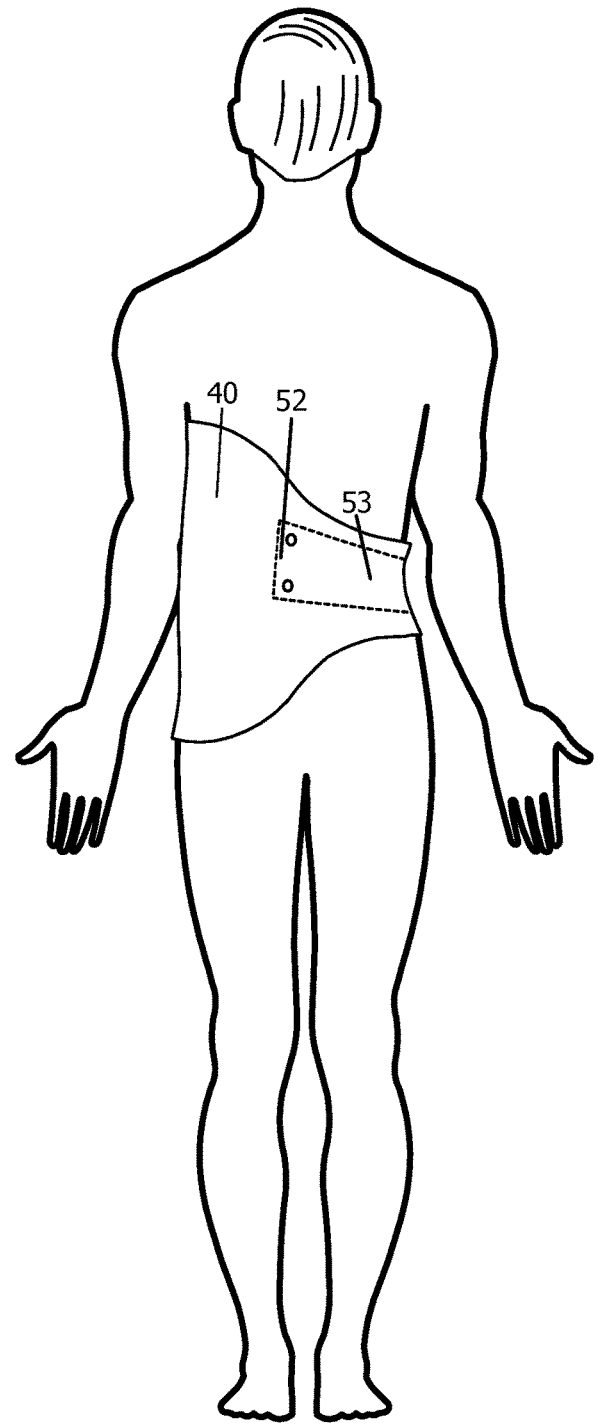
FIG. 10 is a rear view of the spinal orthosis embodiment of FIG. 9 on a wearer.

FIGS. 9-10 depict an adjustment of the spinal orthosis relative to the embodiment in FIG. 8 wherein each feature and component of the embodiment of the spinal orthosis in FIG. 8 is mirrored including but not limited to the first strap 50, the first hole 43 and location thereof, the first bracket 70 and location thereof, the location at which the first end 51 of the first strap fastens to the brace shell 40, and the brace shell properties, shape, and relative proportions. The sagittal plane serves as the mirror plane for this embodiment.

This embodiment of the spinal orthosis may be advantageous for treatment of wearers with a single right scoliosis curve who may possess relatively less upper body strength such as those wearers who are younger or may be of relatively smaller size. This embodiment is worn by the wearer in a manner mirroring that of the embodiment in FIG. 8, wherein the first strap 50 is configured to interface with the right side of the wearer's torso. This embodiment may also provide satisfactory treatment for other conditions and spinal deformations.

Figure 11:
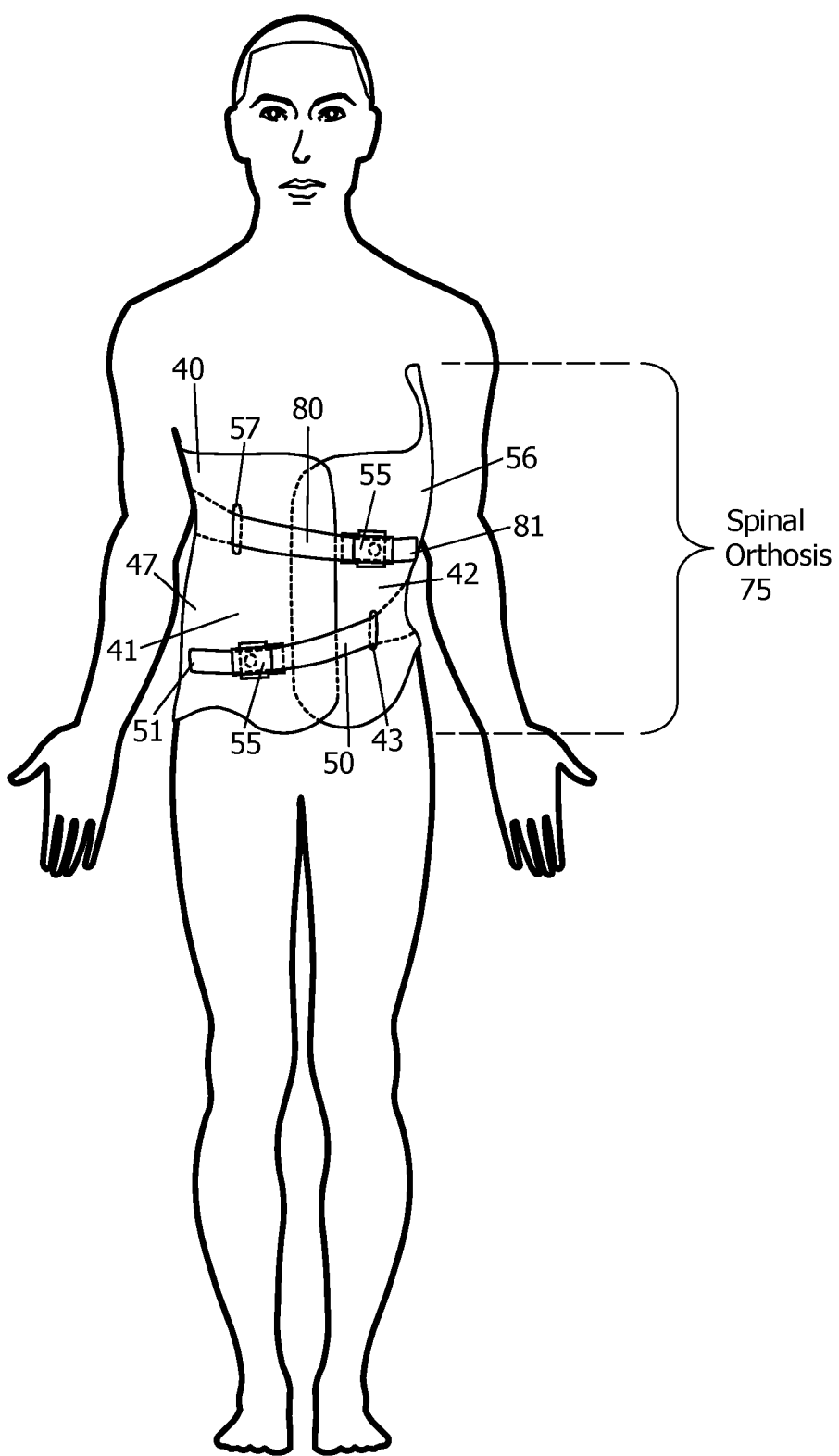
FIG. 11 is a front view of an embodiment of a spinal orthosis comprising a first and second strap on a wearer.
Figure 12:
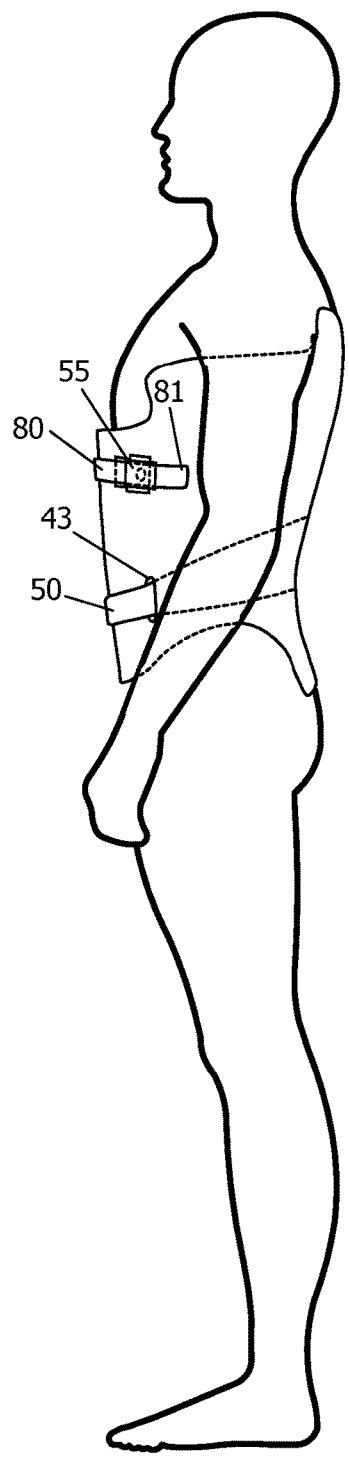
FIG. 12 is a side view of the spinal orthosis embodiment of FIG. 11 on a wearer.
Figure 13:
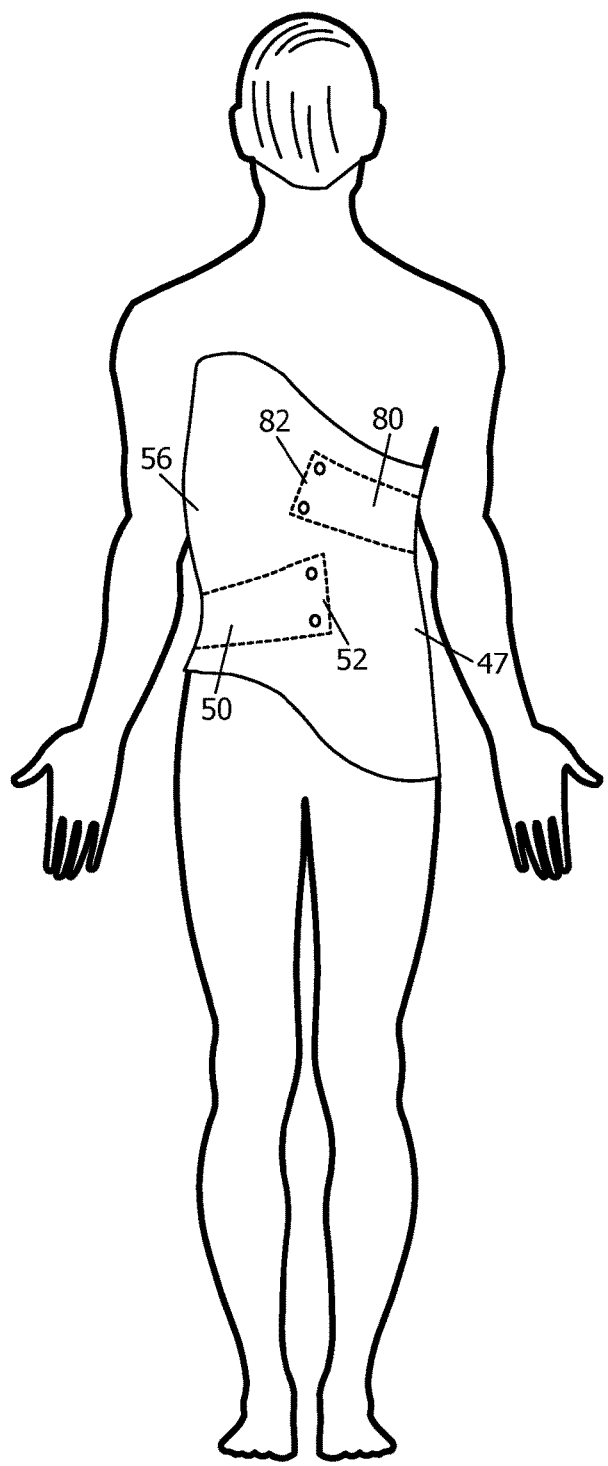
FIG. 13 is a rear view of the spinal orthosis embodiment of FIG. 11 on a wearer.

FIGS. 11-13 show a variation of the embodiment of the spinal orthosis in FIGS. 3-5 that includes a first strap 50, a second strap 80, a first hole 43 and a second hole 57. In this embodiment, the spinal orthosis 75 is configured to align a wearer's spine 35 having a superior scoliosis curve with a right apex 38 and an inferior scoliosis curve with a left apex 37. The second end 52 of the first strap fastens to the brace shell 40 at a location corresponding substantially to the superior end plate of the apical vertebrae 37 of an inferior scoliosis curve to which the first strap 50 is intended to align. The second end 82 of the second strap fastens to the brace shell at a location corresponding substantially to the superior end plate of the apical vertebrae 38 of a superior scoliosis curve to which the second strap 80 is intended to align.

The first strap 50 is configured to extend from its second end 52 inside of at least a portion of the brace shell 40 around at least a portion of the left side of the wearer's torso. The first strap 50 is configured to extend through the first hole 43, the first hole being located on the left side 42 of the anterior portion of the brace shell in a location inferior to that of the second hole 57. The first strap 50 extends through the first hole 43, circumferentially around at least a portion of the outside of the left 42 and right 41 side of the anterior portion of the brace shell. The first end 51 of the first strap detachably fastens to the right side 41 of the anterior portion of the brace shell in a location reachable by the first strap 50 without substantially deviating from its path initiated inside the brace shell 40.

The location of the first hole 43 in the left anterior portion 42 of the brace shell is determined by: placing the hole 43 at a location corresponding to the anterolateral aspect of the wearer's left rib that articulates with the apical vertebrae of the inferior curve if the apical vertebrae is a thoracic vertebrae above T11; or, placing the hole 43 at a location corresponding to just below the anterolateral aspect of the tenth left rib if the apical vertebrae is a lumbar vertebrae or thoracic vertebrae below T10.

The second strap 80 is configured to extend from its second end 82 inside of at least a portion of the brace shell 40 around at least a portion of the right side of the wearer's torso. The second strap 80 is configured to extend through the second hole 57, the second hole being located on the right side 41 of the anterior portion of the brace shell in a location superior to that of the first hole 43. The second strap 80 extends through the second hole 57, circumferentially around at least a portion of the outside of the right 41 and left 42 side of the anterior portion of the brace shell. The first end of the second strap 81 fastens to the left side 42 of the anterior portion of the brace shell in a location reachable by the second strap 80 without substantially deviating from its path initiated inside the brace shell 40.

The location of the second hole 57 in the right anterior portion 41 of the brace shell is determined by: placing the hole 57 at a location corresponding to the anterolateral aspect of the wearer's right rib that articulates with the apical vertebrae of the superior curve if the apical vertebrae is a thoracic vertebrae above T11; or, placing the hole 57 at a location corresponding to just below the anterolateral aspect of the tenth right rib if the apical vertebrae is below T10.

The first and second strap's orientation, when configured according to the aforementioned details, provides corrective forces in an anteromedial direction to the inferior and superior spinal curvatures respectively, when the straps 50, 80 are tensioned and fastened at their first ends 51, 81. The anteromedial forces derotate the spine 30 and translate the spine 30 medially at the apices 37, 38 of the spinal curvatures thereby improving spine alignment.

In a manner substantially similar to that of the embodiment in FIGS. 3-5, the brace shell in this embodiment is shaped to provide adequate space 47 on the side of the brace shell cavity opposite the portion of the first strap 53 located inside the brace shell in order for the wearer's torso to move, unimpeded, into a position of spinal alignment. Likewise, the brace shell 40 in this embodiment is shaped to provide adequate space 56 on the side of the brace shell cavity opposite the portion of the second strap located inside the brace shell 40. The process of shaping brace shells with additional space 47, 56 within specific areas of the brace shell cavity 90 to provide space for the wearer's torso to move into a position of improved alignment is well known to those skilled in the art.

Numerous means of fastening each of the first ends 51, 81 of the first and second straps to the brace shell 40 are readily available and well known to those skilled in the art. Types of fasteners that allow a strap to be routed through the fastener and further tensioned by pulling the end of the strap through the fastener prior to securing the strap are preferred in this application since such fasteners would act as a pulley, closing the split in a brace shell 91 while pulling the strap. One example of, and not an exhaustive list of such a fastener is a cam buckle 55.

The brace shell 40 is shaped to provide the upper point of counter-force in a 3-point system of forces for aligning the superior spinal curvature; and, the lower point of counter-force in a 3-point system of forces for aligning the inferior spinal curvature. The brace shell 40 stabilizes the portions of the spine above the superior spinal curvature and below the inferior spinal curvature while the first and second strap 50 and 80 act as middle points of force for the inferior and superior curves respectively. The first strap also acts as the inferior counter-force for the 3-point system that aligns the superior spinal curvature; the second strap also acts as the superior counter-force for the 3-point system that aligns the inferior spinal curvature.

The process of donning the spinal orthosis 75 on the wearer comprises applying the brace shell 40 around the wearer's torso with the holes 43, 57 and fastening points 52,82 over the anatomical locations to which they correspond. The first strap 50 is tensioned and fastened first. Then, the second strap 80 is tensioned and fastened.

While this embodiment of the spinal orthosis 75 is advantageous when treating wearers with a double scoliosis curve 36 with a superior right curve having a right apex, and an inferior left curve having a left apex, this embodiment may also provide satisfactory treatment for other conditions and spinal deformations.

Figure 14:
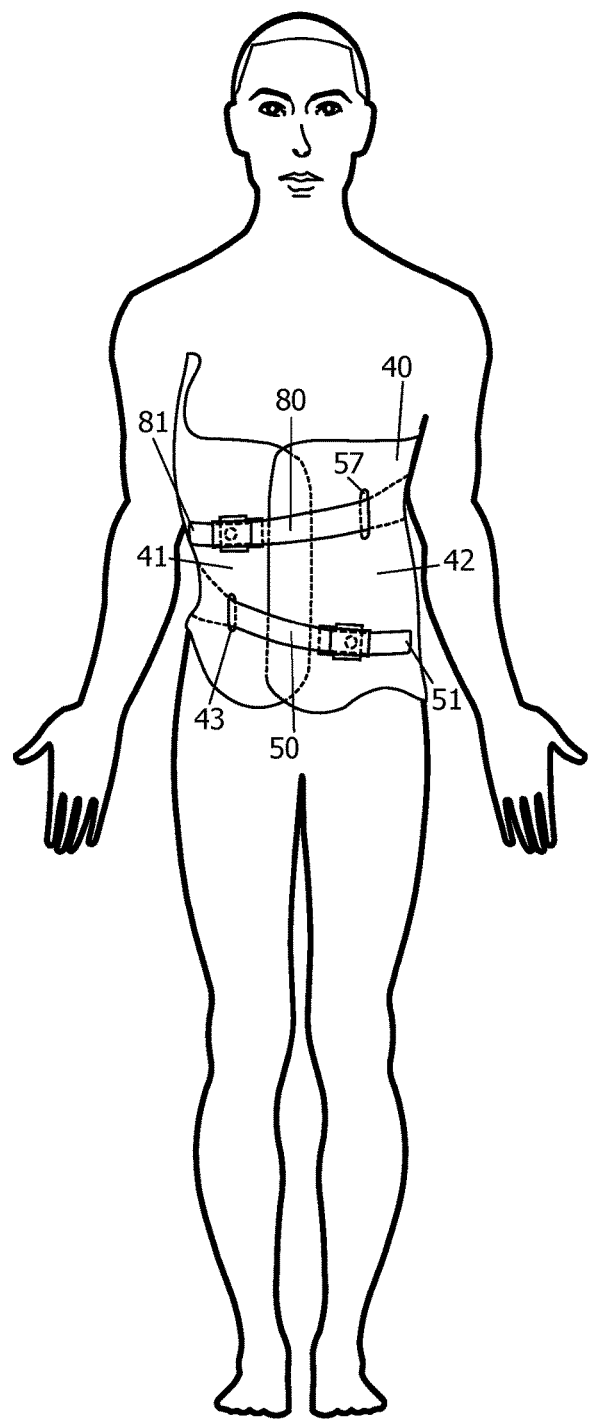
FIG. 14 is a front view of an embodiment of a spinal orthosis on a wearer depicting a mirrored configuration relative to the embodiment of FIG. 11.
Figure 15:
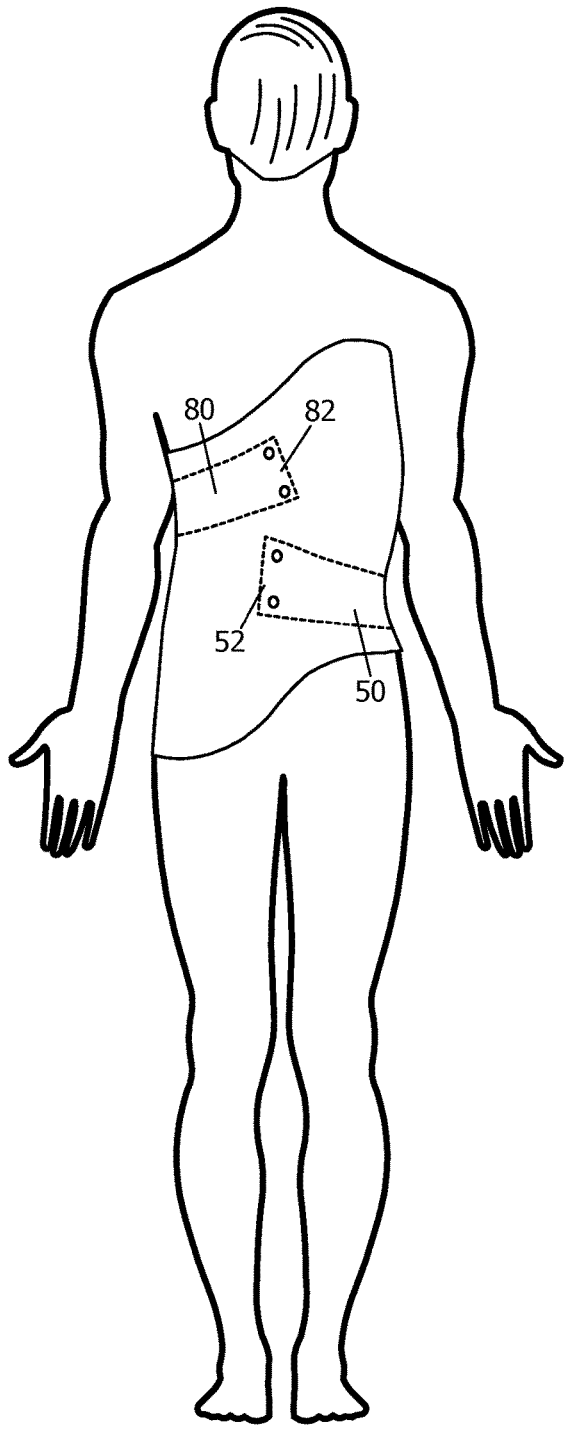
FIG. 15 is a rear view of the spinal orthosis embodiment of FIG. 14 on a wearer.

FIGS. 14-15 depict adjustment of the spinal orthosis relative to the embodiment in FIGS. 11-13 wherein each feature and component of the embodiment in FIGS. 11-13 is mirrored including but not limited to the first 50 and second 80 straps and orientations thereof, the first 43 and second 57 holes and locations thereof, the locations at which the first ends of the first 51 and second 81 straps fasten to the brace shell 40, and the brace shell properties, shape, and relative proportions. The sagittal plane serves as the mirror plane for this depiction.

This embodiment of the spinal orthosis may be advantageous for treatment of wearers with a double scoliosis curve with a superior left curve having a left apex, and an inferior right curve having a right apex. This embodiment is worn by the wearer in a manner mirroring that of the embodiment in FIGS. 11-13, wherein the first strap 50 is configured to interface with the right side of the wearer's torso. The second strap 80 is configured to interface with the left side of the wearer's torso. This embodiment may also provide satisfactory treatment for other conditions and spinal deformations.

Figure 16:
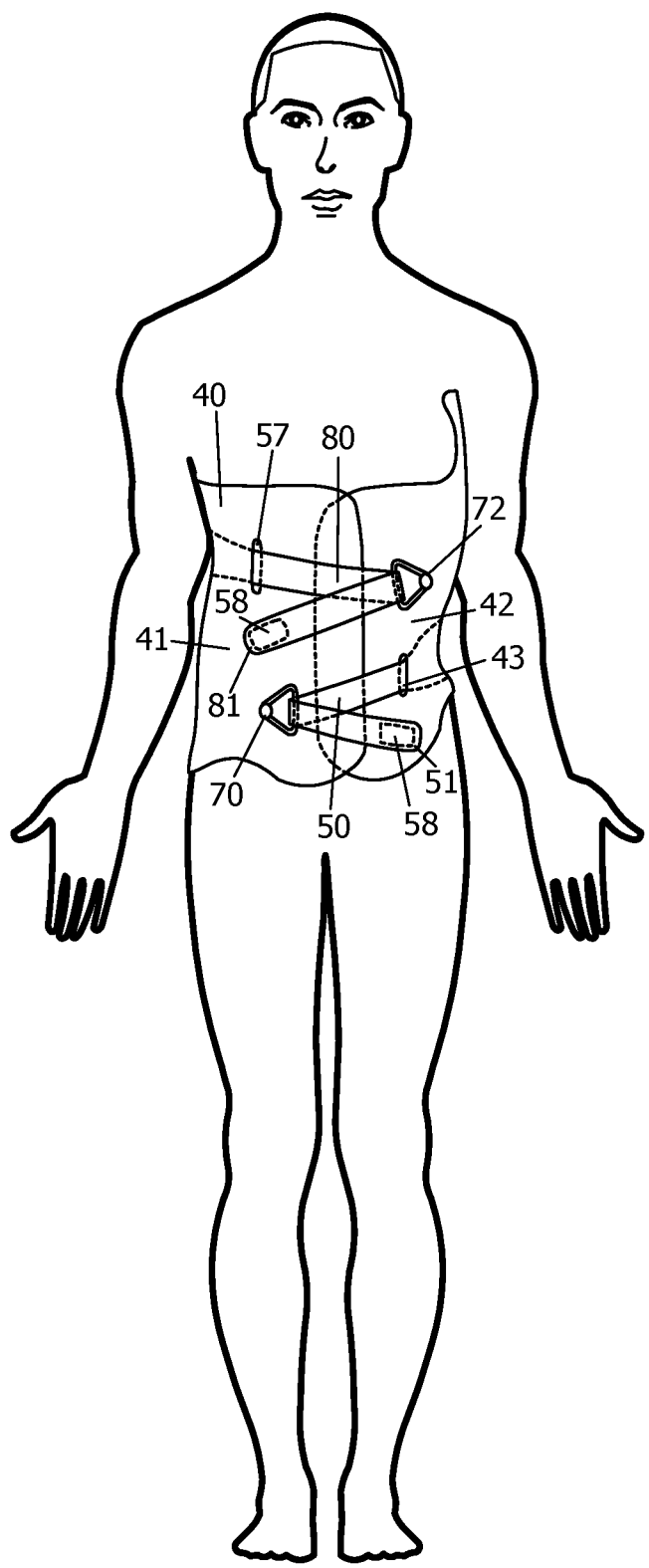
FIG. 16 is a front view of an embodiment of a spinal orthosis on a wearer in which the first and second straps redirect through first and second brackets.

FIG. 16 depicts adjustment of the spinal orthosis relative to the embodiment of FIGS. 11-13 wherein the first strap 50 extends through the first hole 43, across the brace shell split 91, to the right side 41 of the anterior portion of the brace shell, and then redirects through a first bracket 70 back across the brace shell split 91 to the left side 42 of the anterior portion of the brace shell where it detachably fastens to the brace shell 40.

The second strap 80 extends through the second hole 57, being located on the right side 41 of the anterior portion of the brace shell, across the brace shell split 91, to the left side 42 of the anterior portion of the brace shell, and then redirects through a second bracket 72 back across the brace shell split 91 to the right side 41 of the anterior portion of the brace shell where it detachably fastens to the brace shell 40.

The first bracket 70 is fastened to the right side of the anterior portion 41 of the brace shell in a location reachable by the first strap 50 without substantially deviating from its path initiated inside the brace shell 40. Likewise, the second bracket 72 is fastened to the left side of the anterior portion 42 of the brace shell in a location reachable by the second strap 80 without substantially deviating from its path initiated inside the brace shell 40.

Numerous means of detachably fastening each of the first ends of the first 51 and second straps 81 to the brace shell 40 in this embodiment are available and well known to those skilled in the art. Types of fasteners appropriate for use in this application include but are not limited to buckles, ratcheting fasteners, and hook and loop material fasteners 58.

This depiction of the spinal orthosis, relative to the embodiment of FIGS. 11-13, may require relatively less strength to close the brace shell split 91 by pulling and fastening the first and second strap's first ends 51 and 81 as a result of the straps' redirections and extra lengths.

The embodiment of the spinal orthosis in FIG. 16 may be advantageous for treatment of wearers with a double scoliosis curve 36 with a superior right curve having a right apex, and an inferior left curve having a left apex. This embodiment may present further advantage to wearers who possess relatively less upper body strength such as those wearers who are younger or who may be of relatively smaller size. This embodiment may also provide satisfactory treatment for other conditions and spinal deformations.

Figures 17, 18:
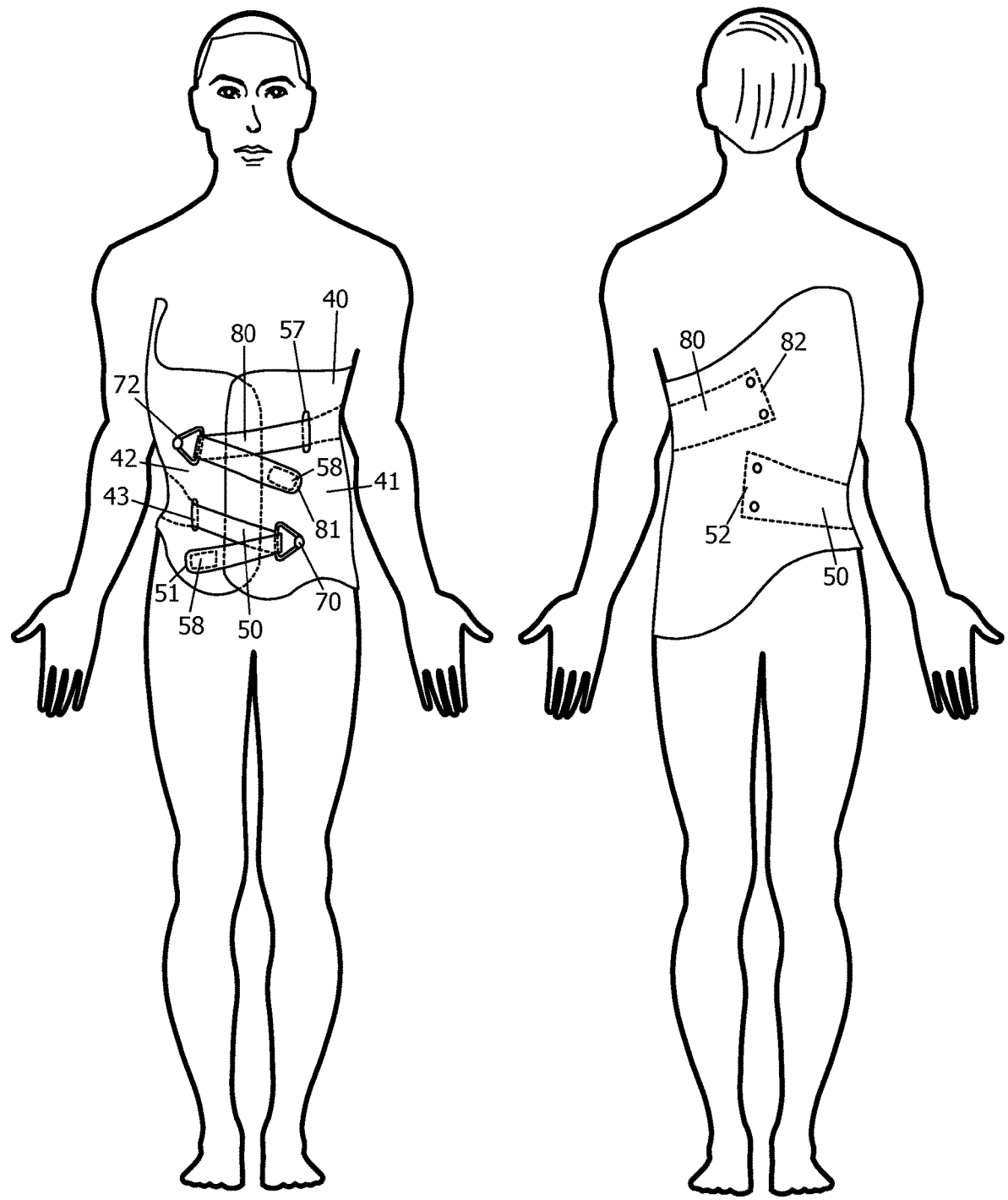
FIG. 17 is a front view of an embodiment of a spinal orthosis on a wearer depicting a mirrored configuration relative to the embodiment of FIG. 16.
FIG. 18 is a rear view of the spinal orthosis embodiment of FIG. 17 on a wearer.
Figure 19:
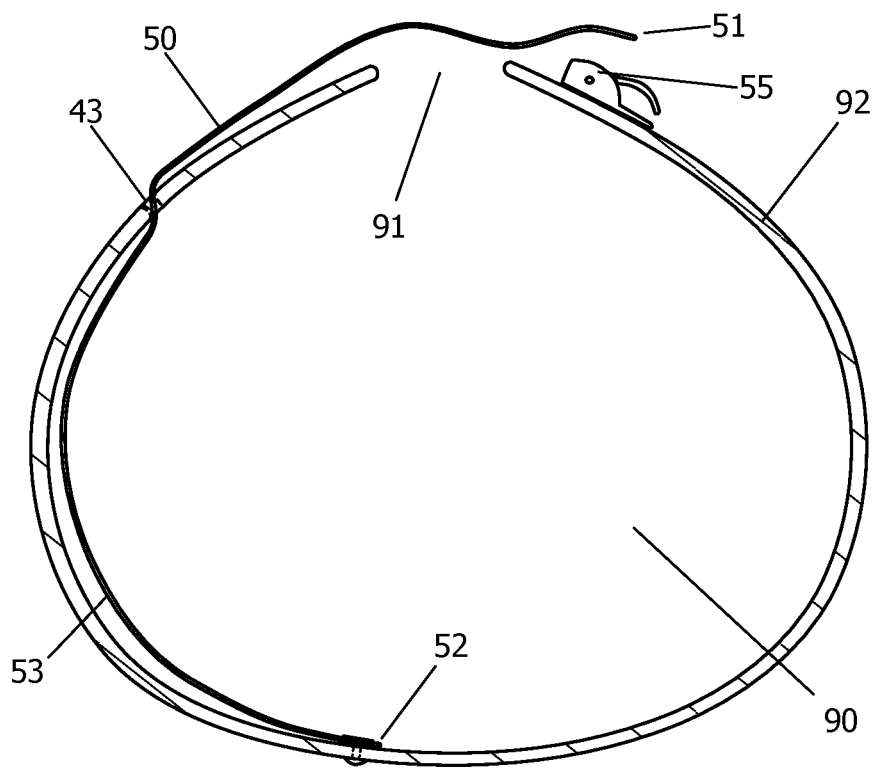
FIG. 19 is a cross sectional view from a top perspective of the spinal orthosis embodiment of FIG. 3 in a relaxed position with a slackened first strap and an open split in the brace shell.
Figure 20:
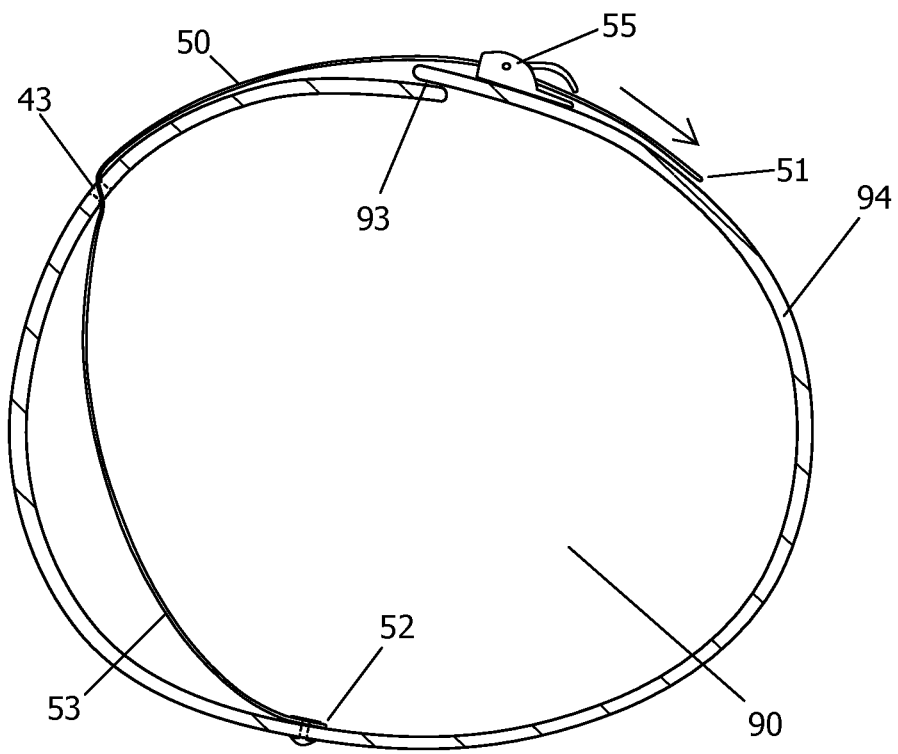
FIG. 20 is a cross sectional view from a top perspective of the spinal orthosis embodiment of FIG. 19 with a tightened first strap and the split in the brace shell relatively closed.

FIGS. 17-18 depict an adjustment of the spinal orthosis relative to the embodiment in FIG. 16 wherein each feature and component of the embodiment in FIG. 16 is mirrored including but not limited to the first 70 and second 72 brackets and locations thereof, the first 50 and second 80 straps and orientations thereof, the first 43 and second 57 holes and locations thereof, the locations at which the first ends of the first 51 and second 81 straps fasten to the brace shell 40, and the brace shell properties, shape, and relative proportions.

This embodiment of the spinal orthosis is worn by the wearer in a manner mirroring that of the embodiment in FIG. 16, wherein the first strap 50 is configured to interface with the right side of the wearer's torso, and the second strap 80 is configured to interface with the left side of the wearer's torso.

The embodiment of the spinal orthosis in FIGS. 17-18 may be advantageous for treatment of wearers with a double scoliosis curve with a superior left curve having a left apex, and an inferior right curve having a right apex. This embodiment may present further advantage to wearer's who may possess relatively less upper body strength such as those wearers who are younger or who may be of relatively smaller size. This embodiment may also provide satisfactory treatment for other conditions and spinal deformations.

Figure 23:
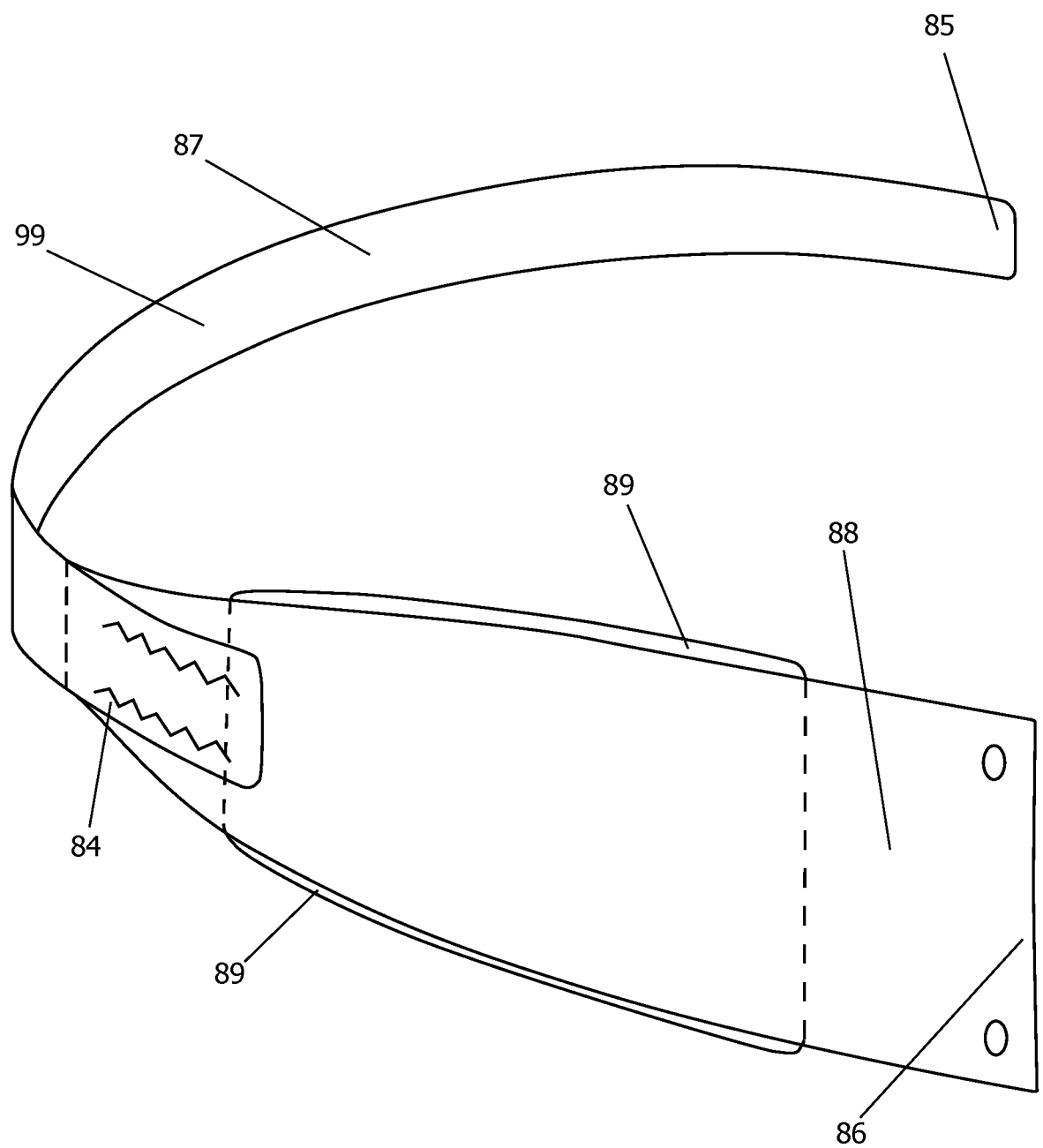
FIG. 23 is a rear view of a strap of an embodiment of the spinal orthosis.

FIG. 23 depicts adjustment of a strap with a combination of different materials comprising the length of the strap. In some embodiments, a strip of low density polyethylene 88 is linked to a strip of polyester webbing 87 via stitching 84 to comprise the strap. The strip of low density polyethylene 88 comprises the section of the strap closest to the strap's second end 86, and the polyester webbing 87 comprises the section of strap closest to the first end of the strap 85.

The low density polyethylene 88 is stiffer than the polyester webbing 87, but more flexible than the brace shell 40. The materials comprising the length of the strap are configured such that the stiffer material, in this case the low density polyethylene 88, is positioned to interface with the wearer's torso. Interfacing with the wearer's torso using a strap comprising a material that's relatively stiffer than polyester webbing 87 provides advantages as the stiffer material will conform less to the wearer's deformities including rib hump 39 in the thoracic region or prominent transverse processes in the lumbar region.

The strip of low density polyethylene 88 is taller relative to the strip of polyester webbing 87 to provide a larger surface area with which to interface with the wearer's torso.

In some embodiments, a portion of the strap comprised of low density polyethylene 88 is configured with a layer of polyethylene foam padding 89 on the strap's inside surface 99. The foam padding 89 in this embodiment has a durometer of 20 shore and is positioned to interface with the wearer's torso.

The inner surface of the foam padding 89 or polyethylene 88 may be convex from superior to inferior to provide a curved shape around which the wearer's torso may bend in the direction opposite the spinal curvature. Using such a composite strap is advantageous for wearers who have prominent deformities, as the foam 89 will distribute the forces placed upon the wearer's torso in the area of the deformity thereby reducing the possibility of focused areas of excessive skin pressure or skin breakdown. The strap configuration of some embodiments may also provide satisfactory treatment of other conditions and spinal deformations.

What is claimed is:

1. A spinal orthosis comprising:
   a brace shell extending from a top end to a bottom end, a split in the brace shell defining an opening that extends from the top end to the bottom end, and a cavity configured to receive a torso of a wearer, the brace shell defining at least one hole that extends radially from the cavity;
   at least one strap configured to extend circumferentially inside of at least a portion of the brace shell, the at least one strap configured to extend through the at least one hole to extend circumferentially around at least a portion of the outside of the brace shell, the at least one strap comprising a first end and a second end, the second end configured to fasten to the brace shell, the first end configured to detachably fasten to the brace shell;
   wherein tensioning of the at least one strap urges the portion of the at least one strap configured to extend circumferentially inside of at least a portion of the brace shell toward the center of the brace shell cavity, and urges a relative closure of the split in the brace shell.

2. The spinal orthosis of claim 1, wherein:
   the brace shell is semi-rigid and further comprises a posterior and an anterior portion;
   the split in the brace shell is located on the anterior portion of the brace shell;
   the anterior portion of the brace comprises a right and a left side separated by the split in the brace shell;
   each of the right side and the left side of the anterior portion of the brace shell have a border comprising the edge of each side of the anterior portion of the brace shell that meets the split in the brace shell;
   the border of the right side and the border of the left side of the anterior portion of the brace shell are separated when the brace shell is in a relaxed state, the brace shell cross-section having substantially a "C"-shape in a relaxed state;
   the brace shell resists being flexed into a relatively closed position in which the borders of the right and the left side of the anterior portion of the brace shell are closer to each other than in the relaxed position of the brace shell, the brace shell storing elastic potential energy when forced into a relatively closed position;
   the second end of the at least one strap is fastened to the brace shell;
   a portion of the at least one strap configured to extend circumferentially around at least a portion of the outside of the brace shell extends across the split in the brace shell;
   the at least one strap comprises an inner surface and an outer surface;
   when the first end of the at least one strap is detachably fastened to the shell of the brace with the brace in a relatively closed position around the wearer's torso, the inner surface of the portion of the at least one strap extending circumferentially inside the brace shell is configured to maintain pressure against the surface of the wearer's torso independent of the wearer's bodily functions that change the diameter of the wearer's torso, wherein:
   when the wearer's torso diameter decreases, the at least one strap is slackened and is drawn from its first end by the elastic potential energy of the brace shell pulling a portion of the at least one strap through the at least one hole toward the outside of the brace shell, thereby shortening the length of strap extending inside the brace shell between the second end of the at least one strap and the at least one hole, resulting in an increase in the brace shell diameter and a relative opening of the split in the brace shell; and
   when the wearer's torso diameter increases, the at least one strap is further tensioned and an additional length is pulled into the cavity of the brace shell through the at least one hole increasing the length of strap extending inside the brace shell between the second end of the at least one strap and the at least one hole thereby decreasing the diameter of the brace shell resulting in a relative closure of the split in the brace shell and an increase in elastic potential energy of the brace shell.

3. The spinal orthosis of claim 2, further comprising at least one bracket configured to fasten to the brace shell, wherein:
   the at least one bracket secures to the at least one strap;
   the portion of the at least one strap configured to extend circumferentially around at least a portion of the outside of the brace shell and across the split in the brace shell extends to the at least one bracket, the at least one strap redirecting from the at least one bracket back across the split in the brace shell.

4. The spinal orthosis of claim 2, wherein:
   the at least one strap is a first strap, the second end of the first strap being fastened to the posterior portion of the brace shell;
   the first strap is configured to extend circumferentially around at least a portion of the left side of the wearer's torso, the first strap configured to extend through the at least one hole, the at least one hole being located on the left side of the anterior portion of the brace shell, the first strap extending through the at least one hole circumferentially around at least a portion of the outside of the left and right side of the anterior portion of the brace shell.

5. The spinal orthosis of claim 2, wherein:
   the at least one strap is a first strap, the second end of the first strap being fastened to the posterior portion of the brace shell;
   the first strap is configured to extend circumferentially around at least a portion of the right side of the wearer's torso, the first strap configured to extend through the at least one hole, the at least one hole being located on the right side of the anterior portion of the brace shell, the first strap extending through the at least one hole circumferentially around at least a portion of the outside of the right and left side of the anterior portion of the brace shell.

6. The spinal orthosis of claim 1, wherein:
   the at least one hole comprises a first hole and a second hole that extend radially from the cavity;
   the at least one strap comprises a first strap and a second strap, the first strap and second strap configured to extend through the first hole and second hole respectively.

7. The spinal orthosis of claim 6, wherein:
the brace shell is semi-rigid and further comprises a posterior and an anterior portion;
the split in the brace shell is located on the anterior portion of the brace shell;
the anterior portion of the brace comprises a right and a left side separated by the split in the brace shell;
each of the right side and the left side of the anterior portion of the brace shell have a border comprising the edge of each side of the anterior portion of the brace shell that meets the split in the brace shell;
the border of the right side and the border of the left side of the anterior portion of the brace shell are separated when the brace shell is in a relaxed state, the brace shell cross-section having substantially a "C"-shape in a relaxed state;
the brace shell resists being flexed into a relatively closed position in which the borders of the right and the left side of the anterior portion of the brace shell are closer to each other than in the brace shell's relaxed position, the brace shell storing elastic potential energy when forced into a relatively closed position;
the second end of the first and second straps are fastened to the brace shell;
a portion of the first strap and second strap configured to extend circumferentially around at least a portion of the outside of the brace shell extend across the split in the brace shell;
each of the first and second straps comprise an inner surface and an outer surface;
when the first end of the first and second straps are detachably fastened to the shell of the brace, the inner surfaces of the portion of the first and second straps extending circumferentially inside of the brace shell are configured to maintain pressure against the surface of the wearer's torso independent of the wearer's bodily functions that change the diameter of the wearer's torso, wherein:
when the wearer's torso diameter decreases, the first and second straps are slackened and drawn from their first ends by the elastic potential energy of the brace shell pulling a portion of the first and second straps through the first and second holes toward the outside of the brace shell, thereby shortening the lengths of strap extending inside the brace shell between the second end of the first and second straps and the first and second holes respectively, resulting in an increase in the brace shell diameter and a relative opening of the split in the brace shell; and
when the wearer's torso diameter increases, the first and second straps are further tensioned and an additional length of each of the first and second straps are pulled into the cavity of the brace shell through the first and second holes respectively increasing the lengths of strap extending inside the brace shell between the second end of the first and second straps and the first and second holes respectively thereby decreasing the diameter of the brace resulting in a relative closure of the split in the brace shell and an increase in stored elastic energy of the brace shell.

8. The spinal orthosis of claim 7, further comprising first and a second bracket configured to fasten to the brace shell, wherein:
the first bracket secures to the first strap;
the second bracket secures to the second strap;
the portion of the first strap configured to extended circumferentially around at least a portion of the outside of the brace shell and across the split in the brace shell extends to the first bracket, the first strap redirecting from the first bracket back across the split in the brace shell, the first end of the first strap configured to fasten to the side of the brace shell defining the first hole;
the portion of the second strap configured to extend circumferentially around at least a portion of the outside of the brace shell and across the split in the brace shell extends to the second bracket, the second strap redirecting from the second bracket back across the split in the brace shell, the first end of the second strap configured to fasten to the side of the brace shell defining the second hole.

9. The spinal orthosis of claim 7, wherein:
the second end of each of the first and second straps are fastened to the posterior portion of the brace shell, the second end of the first strap being fastened in a location inferior to that of the second end of the second strap;
the first strap is configured to extend circumferentially around at least a portion of the left side of the wearer's torso, the first strap configured to extend through the first hole, the first hole being located on the left side of the anterior portion of the brace shell in position inferior to that of the second hole, the first strap extending through the first hole circumferentially around at least a portion of the outside of the left and right side of the anterior portion of the brace shell;
the second strap is configured to extend circumferentially around at least a portion of the right side of the wearer's torso, the second strap configured to extend through the second hole, the second hole being located on the right side of the anterior portion of the brace shell, the second strap extending through the second hole circumferentially around at least a portion of the outside of the right and left side of the anterior portion of the brace shell.

10. The spinal orthosis of claim 7, wherein:
the second end of each of the first and second straps are fastened to the posterior portion of the brace shell, the second end of the first strap being fastened in a location inferior to that of the second end of the second strap;
the first strap is configured to extend circumferentially around at least a portion of the right side of the wearer's torso, the first strap configured to extend through the first hole, the first hole being located on the right side of the anterior portion of the brace shell in position inferior to that of the second hole, the first strap extending through the first hole circumferentially around at least a portion of the outside of the right and left side of the anterior portion of the brace shell;
the second strap is configured to extend circumferentially around at least a portion of the left side of the wearer's torso, the second strap configured to extend through the second hole, the second hole being located on the left side of the anterior portion of the brace shell, the second strap extending through the second hole circumferentially around at least a portion of the outside of the left and right side of the anterior portion of the brace shell.

11. The spinal orthosis of claim 1 wherein:
the section of the brace shell faced by inner surface of the portion of the brace shell inside which the at least one strap is configured to extend is configured to make no contact with the wearer's torso when the brace is applied to the wearer, wherein when the at least one strap is tensioned, the at least one strap may urge the wearer's torso toward the opposite side of the cavity without being impeded by the section of the brace shell faced by the inner surface of the portion of the brace shell inside which the at least one strap is configured to extend.

12. The spinal orthosis of claim 1, wherein:
the brace shell further comprises a posterior and an anterior portion;
the split in the brace shell is located on the anterior portion of the brace shell;
the second end of the at least one strap is fastened to the posterior portion of the brace shell;
the first end of the at least one strap is configured to fasten to the anterior portion of the brace shell at a location inferior to the location that the second end of the at least one strap is fastened, wherein the at least one strap extends from its second end circumferentially inside of at least a portion of the brace shell, through the at least one hole, around at least a portion of the outside of the brace shell to its first end in substantially a helix orientation.

13. The spinal orthosis of claim 1, wherein:
the at least one strap is a combination of different materials secured together along the length of the at least one strap, each material being at least flexible relative to the brace shell.

14. The spinal orthosis of claim 1, wherein at least a portion of the at least one strap is comprised of a composite of two or more constituent materials.

15. The spinal orthosis of claim 14, wherein a layer of constituent material comprising the inner surface of the strap positioned to interface with the wearer's torso is a layer of foam, the layer of foam having a thickness between about 1/16 inch to about 1/2 inch, and a durometer in a range of between about 5 and 75 shore.

* * * * *